(12) United States Patent
Wagner et al.

(10) Patent No.: US 10,548,874 B2
(45) Date of Patent: Feb. 4, 2020

(54) NANOPARTICULATE PHOSPHATE ADSORBENT ON THE BASIS OF MAGHEMITE OR MAGHEMITE/MAGNETITE, PRODUCTION AND USES THEREOF

(71) Applicant: Charite-Universitatsmedizin Berlin, Berlin (DE)

(72) Inventors: Susanne Wagner, Mahlow (DE); Matthias Taupitz, Mahlow (DE); Eyk Schellenberger, Berlin (DE); Jorg Schnorr, Oranienburg (DE); Monika Ebert, Mahlow (DE); Gesche Genter, Berlin (DE); Harald Kratz, Berlin (DE)

(73) Assignee: CHARITE-UNIVERSITATSMEDIZIN BERLIN, Berlin (DE)

( * ) Notice: Subject to any disclaimer, the term of this patent is extended or adjusted under 35 U.S.C. 154(b) by 807 days.

(21) Appl. No.: 14/200,292

(22) Filed: Mar. 7, 2014

(65) Prior Publication Data

US 2014/0248363 A1    Sep. 4, 2014

Related U.S. Application Data

(63) Continuation-in-part of application No. PCT/EP2012/003676, filed on Sep. 3, 2012.

(60) Provisional application No. 61/537,127, filed on Sep. 21, 2011.

(30) Foreign Application Priority Data

Sep. 8, 2011   (DE) .................. 10 2011 112 898

(51) Int. Cl.
| | | |
|---|---|---|
| *C01G 49/02* | (2006.01) | |
| *A61K 9/51* | (2006.01) | |
| *B82Y 30/00* | (2011.01) | |
| *C01G 49/06* | (2006.01) | |
| *A61K 45/06* | (2006.01) | |
| *A61K 31/375* | (2006.01) | |
| *A61K 33/26* | (2006.01) | |
| *A61K 9/50* | (2006.01) | |

(52) U.S. Cl.
CPC .......... *A61K 31/375* (2013.01); *A61K 9/5015* (2013.01); *A61K 9/5115* (2013.01); *A61K 9/5123* (2013.01); *A61K 33/26* (2013.01); *A61K 45/06* (2013.01); *B82Y 30/00* (2013.01); *C01G 49/02* (2013.01); *C01G 49/06* (2013.01); *C01P 2002/32* (2013.01); *C01P 2002/60* (2013.01); *C01P 2004/04* (2013.01); *C01P 2004/64* (2013.01)

(58) Field of Classification Search
CPC .......... A61K 9/51; A61K 45/06; C01G 49/02; C01G 49/06; B82Y 30/00

USPC .......................................... 424/489
See application file for complete search history.

(56) References Cited

U.S. PATENT DOCUMENTS

| | | | |
|---|---|---|---|
| 4,501,726 A | 2/1985 | Schroder et al. | |
| 6,926,912 B1 | 8/2005 | Roberts et al. | |
| 2003/0185757 A1* | 10/2003 | Kresse | A61K 9/5115 424/9.32 |
| 2008/0268061 A1* | 10/2008 | Jordan | A61K 9/0009 514/1.1 |
| 2009/0309597 A1 | 12/2009 | Horak et al. | |
| 2010/0166870 A1* | 7/2010 | Iyer | A61K 47/48861 424/490 |
| 2011/0086097 A1* | 4/2011 | Kaufmann | A61K 33/26 424/474 |

FOREIGN PATENT DOCUMENTS

| | | |
|---|---|---|
| DE | 3508000 | 9/1986 |
| DE | 4325386 | 1/1995 |
| EP | 0525199 | 2/1993 |
| WO | 9201458 | 2/1992 |
| WO | 9505669 | 2/1995 |
| WO | 2006000547 | 1/2006 |
| WO | 2007095871 | 8/2007 |

OTHER PUBLICATIONS

Boyer et al., "The design and utility of polymer-stabilized iron-oxide nanoparticles for naomedicine applications", NPG Asia Materials (Jan. 1, 2010) 2(1): 23-30.

De Vicente et al., "On the use of magnetic nano and microparticles for lake restoration", Journal of Hazardous Materials (Sep. 15, 2010) 181(1-3): 375-381.

Horak et al., "D-Mannose-modified iron oxide nanoparticles for stem cell labeling", Bioconjugate Chemistry (May 3, 2007) 18(3): 1043-1802.

Sun et al., "Size-controlled synthesis of magnetite (Fe3O4) nanoparticles coated with glucose and gluconic acid from a single Fe(III) precursor by a sucrose biofunctional hydrothermal method", Journal of Physical Chemistry Part C: Nanomaterials and Interfaces (2009) 113(36): 16002-16008.

(Continued)

*Primary Examiner* — Adam C Milligan
(74) *Attorney, Agent, or Firm* — Fox Rothschild LLP

(57) ABSTRACT

The present invention relates to a phosphate adsorbent on the basis of maghemite or maghemite/magnetite comprising (i) an iron oxide core comprising a crystal structure of inverse spinel iron oxide, (ii) a coating selected from monomeric carbohydrates, in particular monosaccharides or disaccharides, alditols, or mixtures thereof, and/or (iii) a pharmaceutical excipient selected from polymeric carbohydrates, wherein the phosphate adsorbent has the form of nanoparticles with a particle size of the iron oxide core (i) of less than 20 nm. The present invention further relates to a method for the production of a phosphate adsorbent on the basis of maghemite or maghemite/magnetite, to pharmaceutical compositions comprising the phosphate adsorbent, and to medical uses thereof, especially for the prevention and/or treatment of hyperphosphatemia.

23 Claims, 6 Drawing Sheets

(56) References Cited

OTHER PUBLICATIONS

Figure 1:
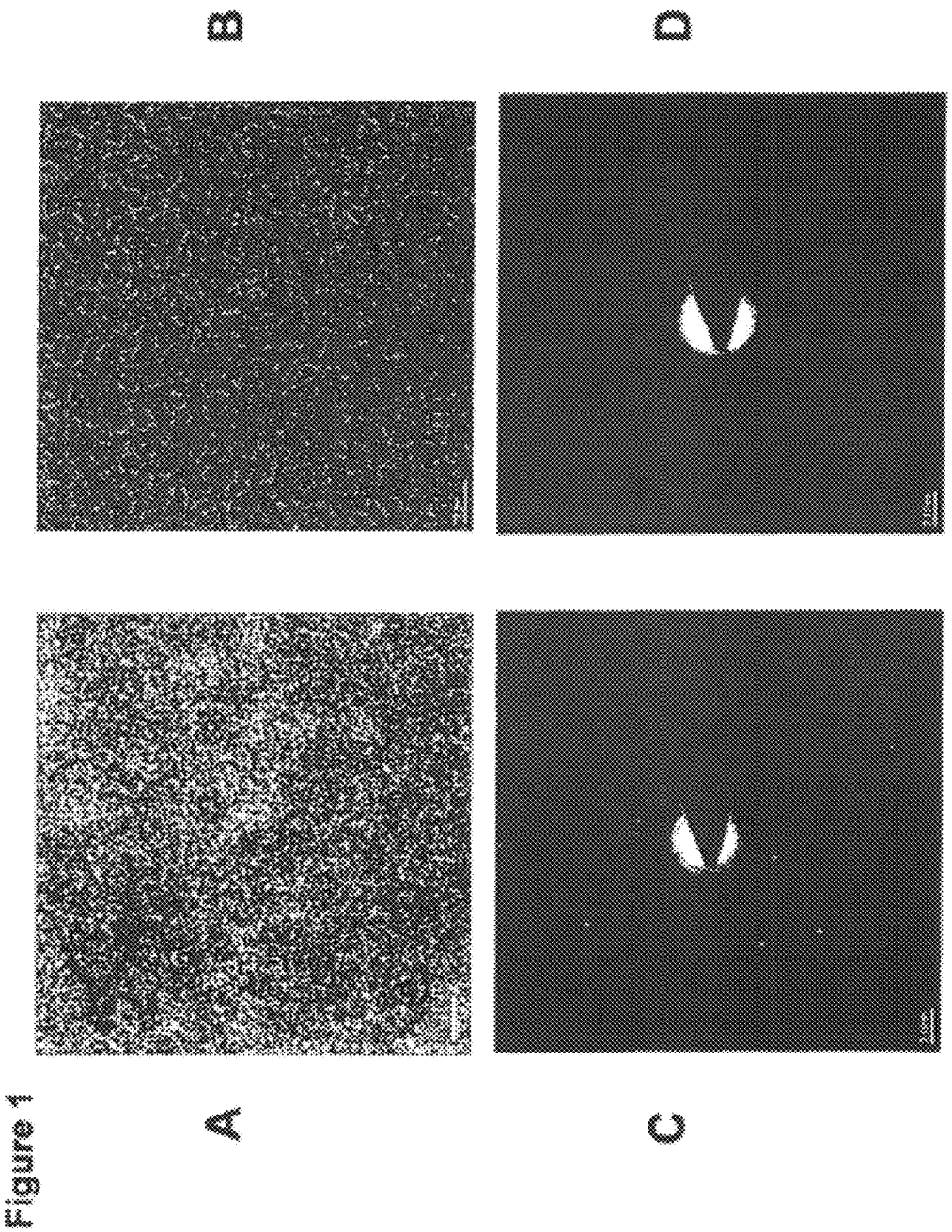

Teja et al., "Synthesis, properties, and applications of magnetic iron oxide nanoparticles", Progress in Crystal Growth and Characterization of Materials (Mar. 1, 2009) 55(1-2): 22-45.

* cited by examiner

TEM transmission electron microscopy
high crystallinity, nanoparticles < 5 nm d(hkl)-values:
0.151nm → (440)
0.164nm → (511)
0.214nm → (400)
0.254nm → (311)
0.297nm → (220)

SAED - selected area electron diffraction good match with reference diffraction data for maghemite-magnetite with card
No 11-0614 JCPDS - International Centre for Diffraction Data

NANOPARTICULATE PHOSPHATE ADSORBENT ON THE BASIS OF MAGHEMITE OR MAGHEMITE/MAGNETITE, PRODUCTION AND USES THEREOF

CROSS-REFERENCE TO RELATED APPLICATIONS

This application is a continuation-in-part of International Application No. PCT/EP2012/003676, filed Sep. 3, 2012, which claims priority to German Application No. 10 2011 112 898.4, filed Sep. 8, 2011, and U.S. Provisional Application No. 61/537,127, filed Sep. 21, 2011, which are hereby incorporated herein by reference in their entireties.

The present invention relates to a phosphate adsorbent on the basis of maghemite or maghemite/magnetite comprising (i) an iron oxide core comprising a crystal structure of inverse spinel iron oxide, (ii) a coating selected from monomeric carbohydrates, in particular monosaccharides or disaccharides, alditols, or mixtures thereof, and/or (iii) a pharmaceutical excipient selected from polymeric carbohydrates, wherein the phosphate adsorbent has the form of nanoparticles with a particle size of the iron oxide core (i) of less than 20 nm. The present invention further relates to a method for the production of a phosphate adsorbent on the basis of maghemite or maghemite/magnetite, to pharmaceutical compositions comprising the phosphate adsorbent, and to medical uses thereof, especially for the prevention and/or treatment of hyperphosphatemia.

BACKGROUND OF THE INVENTION

Patients with impaired renal function develop an abnormal phosphate metabolism. The pathomechanism of hyperphosphatemia in patients with reduced renal function is a complex dysregulation of glomerular filtration, tubular reabsorption, and release from bone caused by a hormonal imbalance. In conjunction with calcium imbalance, hyperphosphatemia increases the risk of cardiovascular disease in patients with impaired renal function. Hyperphosphatemia promotes arterial calcification, increasing the risk of myocardial infarction and stroke in these patients (Hruska et al., 2008).

In early renal dysfunction, hyperphosphatemia can be addressed by reducing dietary phosphate intake, but this measure has the disadvantage of being associated with a deficient uptake of essential nutritional components. Therefore drugs are available for treating hyperphosphatemia by reducing phosphate absorption from food. These drugs can be taken orally and bind free phosphate in the gastrointestinal tract, forming insoluble complexes or aggregates that are excreted with the feces (Coladonato, 2005).

Since patients with impaired renal function require lifelong medication for controlling hyperphosphatemia, there are three basic requirements a phosphate binder must meet:

1) The drug must be safe and ideally should have no adverse effects.

2) Phosphate binding must be high relative to dose.

3) Costs must be low so that the drug is available to all patients who need it.

The most common drugs that bind phosphate in the gastrointestinal tract are based on calcium salts such as calcium acetate and calcium carbonate. Calcium-based phosphate binders are inexpensive but have considerable adverse effects, most notably an increase in calcium serum levels, which in turn accelerates vascular calcification. In advanced kidney failure, adequate control of hyperphosphatemia using calcium-based phosphate binders can only be achieved at the cost of considerable adverse effects.

Sevelamer, which is based on polyallylamine, is more effective and is better tolerated. However, current reimbursement practices in the healthcare sector preclude lifelong treatment of all patients with this drug.

Serum phosphate levels can be lowered most effectively by aluminium hydroxide. This agent is only approved for short-term use in lowering very high serum phosphate levels. Aluminium is absorbed in the gastrointestinal tract, and this absorption has been shown to be associated with encephalopathy and bone demineralization (Wills and Savory, 1989).

Lanthanum carbonate is an effective oral phosphate binder and is available at a reasonable price. However, this drug is associated with predominantly gastrointestinal adverse effects, including obstipation, which requires discontinuation of lanthanum carbonate and switching to an alternative phosphate binder. Moreover, it is assumed that small amounts of lanthanum ions are absorbed in the gastrointestinal tract, contributing to the induction of lanthanum-associated nephrogenic systemic fibrosis. This new condition has only been observed in patients with reduced kidney function who received a gadolinium-based contrast agent for magnetic resonance imaging. In these patients, the longer residence time of the contrast agent in the body leads to release of the lanthanide gadolinium from the contrast agent complex, causing therapy-refractory inflammation of connective tissue structures throughout the body. Nephrogenic systemic fibrosis has so far only been observed in countries where the lanthanum-based phosphate binder Fosrenol is approved, suggesting a synergistic effect of both lanthanides (Brambilla et al., 2008).

New phosphate binders on the basis of iron oxide crystals that can be administered orally are currently undergoing clinical testing of effectiveness. These include ferrihydrite, iron hydroxide, and iron oxyhydroxides such as goethite (alpha-iron oxyhydroxide), akaganeite (beta-oxyhydroxide), and lepidocrocite (gamma-iron oxyhydroxide).

WO 92/01458 describes a method for controlling serum phosphate levels and for treating and preventing hyperphosphatemia. The method consists in oral administration of phosphate-binding oxy-iron compounds (iron oxides and iron oxy-hydroxides), especially synthetic ferrihydrite ($Fe_5O_7(OH)$), for inhibiting phosphate uptake from food.

WO 2006/000547 A2 describes an iron-hydroxide-based phosphate adsorbent prepared from iron(III) sulfate and/or iron(II) nitrate.

WO 2008/071747 A1 discloses a phosphate adsorbent on the basis of polynuclear iron(III) oxide-hydroxide and a soluble carbohydrate partially incorporated into the polynuclear iron(III) oxide-hydroxide and further comprising an adsorbent base material, preferably an insoluble carbohydrate, which is intended for treatment of hyperphosphatemia.

Iron(III) ions are a further basis for metal-based phosphate adsorbers. In experimental studies a high phosphorus binding capacity was found for iron(III) citrate, iron(III) chloride or iron(III) ammonium citrate (Hsu et al, 1999). The production and the use of a pharmaceutical grade iron(III) citrate as an oral phosphate binding drug to treat elevated serum phosphate levels has been laid down by Kwok et al. in U.S. Pat. No. 7,767,851 B2. However, a major drawback of highly soluble iron salts or chelates is the release of free iron ions, leading biochemically to oxidative stress with a high risk of iron toxicity (Somers, 1947). Additionally in patients treated against hyperphosphatemia nearly a life long there is the risk of systemic iron overload due to intestinal iron resorption of the free iron ions, which has been shown for iron(III) citrate (Heinrich, 1987). This results in a limited risk to benefit ratio for these type of iron compounds as phosphate adsorbers.

From geological research and waste water processing, the phosphate-binding capacity of iron oxides, iron hydroxides, and iron oxyhydroxides is known in the art (Daou et al., 2007).

US 2009/0309597 A1 discloses superparamagnetic nanoparticle probes based on iron oxides, such as magnetite or maghemite, with modified surface, coated with mono-, di- or polysaccharides or with amino acids or poly(amino acid)s or with synthetic polymers based on (meth)acrylic acid and their derivatives, which form a colloid consisting of particles with an average size of 0.5-30 nm, having an iron content of 70-99.9 wt. %, preferably 90 wt. %, and having a content of modification agent of 0.1-30 wt. %, preferably 10 wt. %. The nanoparticle probes are suitable as diagnostic probes, such as for the in vitro labelling of cells.

EP 0 525 199 A1 discloses compositions containing ultrafine particles of a magnetic metal oxide, which comprise an aqueous sol of a composite consisting of the ultrafine particles and a polysaccharide, its derivative and/or a protein, and an organic monocarboxylic acid. The compositions are suitable as MRI contrast agents.

There is a need in the prior art for improved phosphate-binding agents and methods of administration.

The present invention therefore aims to provide efficient, easy to manufacture, and well tolerated oral phosphate binders that, among other things, can improve the treatment of hyperphosphatemia.

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Numbers or other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "2 to 20 nm" should be interpreted to include not only the explicitly recited values of 2 to 20, but also include individual values and sub-ranges within the indicated range. Thus, included in this numerical range are individual values such as 2, 3, 4, 5, 6, 7, 8, 9, 10, 11, 12, 13, 14, 15, 16, 17, 18, 19, 20 nm and sub-ranges such as from 2 to 5 nm, from 2 to 10 nm, from 2 to 8 nm etc. As an illustration, a numerical range of "about 3 to 50 wt-%" should be interpreted to include not only the explicitly recited values of 3 to 50, but also include individual values and sub-ranges within the indicated range. Thus, included in this numerical range are individual values such as 3, 4, 5, 6, 7, ... 48, 49, 50 and sub-ranges such as from 3 to 45, 5 to 45, 10 to 45, 15 to 45, 3 to 40, 5 to 40, 10 to 40, 15 to 40, 3 to 35, 5 to 35, 10 to 35, 15 to 35, etc. This same principle applies to ranges reciting only one numerical value. Furthermore, such an interpretation should apply regardless of the breadth of the range or the characteristics being described.

Phosphate Adsorbent with Inverse Spinel Iron Oxide Core and Coating(s)

The object is solved according to the invention by providing a phosphate adsorbent comprising (i) an iron oxide core comprising an inverse spinel iron oxide crystal structure, (ii) a coating selected from (a) monosaccharides or disaccharides, or (b) alditols, or mixtures thereof, and/or (iii) a pharmaceutical excipient selected from polymeric carbohydrates.

The phosphate adsorbent according to the invention has the form of nanoparticles.

The nanoparticles have a particle size of the iron oxide core (i) of less than/smaller than 20 nm, preferably less than/smaller than 10 mm.

The nanoparticles have a particle size of the iron core (i) of preferably 2 to 20 nm, more preferably 2 to 5 nm.

The phosphate adsorbent according to the present invention is based on maghemite or a mixture of maghemite and magnetite.

The phosphate adsorbent according to the present invention is not based on iron citrate or ferric citrate.

The use of phosphate binders on the basis of iron oxide crystals has several advantages for patients with impaired renal function. Iron-based medications for treating hyperphosphatemia can be manufactured at low cost, and adverse events are not likely to occur. Patients on hemodialysis generally require iron replacement therapy since considerable amounts of iron are eliminated by hemodialysis treatment. Hence, potential gastrointestinal absorption of small amounts of iron is not an undesired adverse effect. On the contrary, it even has a therapeutic benefit in this patient population compared with the undesired risks associated with aluminium, calcium, or lanthanide from other phosphate binders.

There are some basic requirements for a phosphate binder based on iron oxide crystals:

1) The type of iron oxide crystal used has to ensure optimal phosphate adsorption.

2) The crystallite size has to be as small as possible to provide a large adsorptive surface area.

3) The individual crystals should preferably have a coating that can be displaced by phosphate, while providing long enough stability in the digestive tract.

4) It is preferred that a galenic formulation and the dosage form ensure optimal mixture of the iron-oxide-crystal-based phosphate adsorbent with body fluids and food components in the digestive tract.

The phosphate adsorbent according to the invention preferably has an iron content which is about 3 to 50 wt-% of total weight of the phosphate adsorbent,
3 to 45 wt-% of total weight of the phosphate adsorbent,
5 to 45 wt-% of total weight of the phosphate adsorbent,
10 to 45 wt-% of total weight of the phosphate adsorbent,
15 to 45 wt-% of total weight of the phosphate adsorbent,
3 to 40 wt-% of total weight of the phosphate adsorbent,
5 to 40 wt-% of total weight of the phosphate adsorbent,
10 to 40 wt-% of total weight of the phosphate adsorbent,
15 to 40 wt-% of total weight of the phosphate adsorbent,
3 to 35 wt-% of total weight of the phosphate adsorbent, 5 to 35 wt-% of total weight of the phosphate adsorbent,
10 to 35 wt-% of total weight of the phosphate adsorbent.
15 to 35 wt-% of total weight of the phosphate adsorbent, (i) Iron Oxide Core The iron oxide core of the phosphate adsorbent according to the present invention comprises an inverse spinel iron oxide crystal structure.

Iron oxide crystals of the inverse spinel type have the highest phosphate binding capacity of all iron oxides in relation to the crystal surface area (Daou et al., 2007, Barber 2002). There are only two inverse spinel iron oxides: magnetite ($Fe_3O_4$) and its oxidized form, maghemite (gamma-$Fe_2O_3$). It is known that maghemite has a higher phosphate-binding capacity than magnetite in relation to the surface area available for adsorption.

The use of iron oxides of the inverse spinel type for phosphate adsorption from food or fluids in the digestive tract has not been investigated or even considered. Suitable particle dispersions on the basis of inverse spinel iron oxides are not known, have not been manufactured, and/or have not been tested for this purpose.

Inverse spinel iron oxides have a crystal structure that is distinct from that of all other iron oxides. This structure is characterized by cubic close packed oxygen atoms with tetrahedral and octahedral positions for iron ions according to crystallographic nomenclature. One unit cell consists of 32 oxide ions with 64 tetrahedal sites and 32 octahedral sites. In the inverse spinel iron oxide magnetite, ferric ions occupy ⅛ of the tetrahedral sites and ¼ of the octahedral sites. In maghemite, the oxidized form of magnetite, the arrangement of oxide ions is the same as in magnetite. However, in contrast to magnetite, ⅛ of tetrahedral sites and ½ of octahedral sites are occupied by 21⅓ ferric ions with 2⅓ of sites remaining vacant. Hence, maghemite is a defect inverse spinel iron oxide in relation to magnetite.

In a preferred embodiment, the phosphate adsorbent according to the invention is monocrystalline.

A monocrystal, or single crystal, is a macroscopic crystal characterized by an entirely regular arrangement of its components (atoms, ions, or molecules). This arrangement distinguishes a monocrystal from polycrystalline aggregates, twinned crystals, or amorphous substances.

In a preferred embodiment, the phosphate adsorbent according to the invention is mononuclear. According to the present invention, "mononuclear" is used to mean that the monocrystals do not aggregate. This is important to ensure that the required or desired surface area is available for phosphate adsorption.

In a preferred embodiment, the phosphate adsorbent according to the invention is monodisperse, meaning that the nanoparticle sizes are within a predefined size range (especially a particle size of the iron oxide core (i) of less than 20 nm, preferably of less than 10 nm; especially a particle size of the iron oxide core (i) of preferably 2 to 20 nm, more preferably 2 to 5 nm).

In a preferred embodiment, the iron oxide core (i) of the phosphate adsorbent according to the invention comprises (nanoscale) inverse spinel iron oxide with over 90% having the same crystallite size (i.e., a particle size of the iron oxide core (i) of less than 10 nm, preferably less than 5 nm, more preferably 2 to 5 nm).

In a preferred embodiment, the iron oxide core (i) of the phosphate adsorbent according to the invention consists of (nanoscale) inverse spinel iron oxide with over 90% having the same crystallite size (i.e., a particle size of the iron oxide core (i) of less than 10 nm, preferably less than 5 nm, more preferably 2 to 5 nm).

In a preferred embodiment, the iron oxide core (i) comprises monocrystalline maghemite with less than 20 weight percent of magnetite or consists of monocrystalline maghemite with less than 20 weight percent of magnetite.

Pure magnetite has 30% ferrous ions expressed in relation to total iron (molar ratio). Expressing the proportion of ferrous iron in relation to total iron as a molar ratio is equivalent to giving the percentage weight since ferrous iron has one electron more than ferric iron, which is negligible relative to total mass.

It is preferred that the iron oxide core (i) according to the invention comprises inverse spinel iron oxide with less than 20% ferrous ions in relation to total iron (molar ratio), preferably less than 15%, more preferably less than 10%, even more preferably less than 5% or less than 3% (molar ratio). In a preferred embodiment, the proportion of ferrous iron is less than 5%, more preferably less than 3% (molar ratio).

In one embodiment, the iron oxide core (i) further comprises hematite, goethite, lepidocrocite, akaganeite, and/or ferrihydrite in a weight proportion of less than 20% in relation to total iron.

The phosphate adsorbent according to the invention is available in the following embodiments:
 Iron oxide core (i) with coating (ii);
 Iron oxide core (i) with pharmaceutical excipient (iii);
 Iron oxide core (i) with coating (ii) and pharmaceutical excipient (iii).

(ii) Primary Coating

The phosphate adsorbent according to the invention preferably comprises a coating (ii) comprising:
 (a) mono- or disaccharides,
 (b) alditols,
 or mixtures thereof.

The coating (ii) is the primary coating of the iron oxide cores (i).

The individual crystals (i.e., the iron oxide cores (i)) require a sheath/coating that can be displaced by phosphate while providing long enough stability in the gastrointestinal tract.

The surface of iron oxides of the inverse spinel type is highly adsorptive, and the particles aggregate in aqueous dispersion when they lack a suitable coating. This is why the individual crystals require a coating in order to be used as a phosphate binder in the gastrointestinal tract. A major hypothetical prerequisite is that the coating should ideally only be displaceable by phosphate and interact as little as possible with other substances and molecules present in the fluids of the gastrointestinal tract.

In addition to these requirements regarding the coating, the individual crystals must be as small as possible to maximize the adsorptive surface area relative to the total iron content. Known and commercially available drugs on the basis of inverse spinel iron oxide such as Resovist®, with ferucarbotran as the active agent, and Feraheme®, with ferumoxytol as the active agent, are based on maghemite crystals with a coat of polymer carboxydextran, and, in the form of highly stable dispersions, are approved for intravenous administration as a contrast agent for magnetic resonance imaging (Resovist®) or as a therapeutic drug for treating iron deficiency anemia (Feraheme®). In addition, numerous production methods and preparations of inverse spinel iron oxides with crystallite sizes of less than 20 nm are known. These are kept in stable aqueous dispersion by highly stabilizing coatings consisting of citrate, tartrate, glucuronic acid, or glutamic acid and can also be administered intravenously. In comparative examples 3 and 4, these highly stable dispersions show very strong interaction between the coating and the iron oxide core with only little displacement by phosphate. This is why these inverse spinel iron oxides with very stable coatings, which are already in use as drugs in humans or under clinical investigation for use in humans, appear not to be well suited for controlling hyperphosphatemia by adsorbing phosphate in the digestive tract.

The aliphatic or cyclic mono- or disaccharides (a) of the coating according to the invention (ii) are preferably selected from mono- or disaccharides of aliphatic and/or aromatic hexoses or pentoses. These are further preferably selected from mannose, saccharose, fructose, fucose, trehalose, glucose, rhamnose, galactose, maltose, and arabinose.

A preferred embodiment of the (primary) coating (ii) comprises mannose, maltose, and/or saccharose, or consists of mannose, maltose, and/or saccharose.

The alditols (b), or sugar alcohols, of the coating (ii) according to the invention are preferably selected from mannitol, sorbitol, isomalt, threitol, lactitol, xylitol, arabitol, erythritol, and glycerol, more preferably from mannitol.

In a preferred embodiment, the (primary) coating (ii) does not comprise or consist of citrate, tartrate, glucuronic acid, or glutamic acid. These compounds/substances have a carboxyl group, which results in too strong bonding to the surface of the iron oxide cores, precluding adequate displacement by phosphate.

In a preferred embodiment, the (primary) coating (ii) does not comprise or consist of saturated or unsaturated fatty acids or tensides.

Also preferred are mixtures of aliphatic or cyclic mono- or disaccharides (a) with alditols (b).

Mixtures of aliphatic or cyclic mono- or disaccharides with mannitol are particularly preferred for intravenous administration.

In a preferred embodiment, the coating (ii) is in excess of the binding sites on the iron oxide crystal surface (of the iron oxide cores (i)).

The coating (ii) prevents mutual aggregation of the iron oxide crystals and undesired interactions with components of physiological fluids in the gastrointestinal tract and food components in the gastrointestinal tract while at the same time being displaceable by inorganic phosphate. The coating (ii) interacts with the iron oxide surface in the form of van der Waals forces, electrostatic attraction, salt formation, or complex formation. In order to ensure adequate enclosure by the coating (ii), a molar excess of the coating (ii) in relation to the binding sites on the iron oxide crystal surface in accordance with the thermodynamic behavior of said interactions must be available during production of the iron-based phosphate adsorbent according to the invention and after resuspension for use as a drug.

This is reliably accomplished during the production of the phosphate adsorbent according to the invention by:

(1) adding the coating (ii) during the crystallization process in a ratio to total iron (sum of ferrous and ferric ions) at a molar excess of at least 1.2 (up to 10-fold excess), preferably 2- to 5-fold molar excess, for example 3-fold excess (see example 1);

(2) optionally adding the coating (ii) after the purification steps (dialysis, ultrafiltration, centrifugation, diafiltration) in an amount that corresponds to between 5 and 20% of the amount initially used in the primary reaction mixture.

(iii) Pharmaceutical Excipient

The phosphate adsorbent according to the invention preferably comprises a pharmaceutical excipient (iii).

The excipient according to the invention (iii) serves as a (secondary) coating and for the pharmaceutical formulation of the phosphate adsorbent according to the invention.

The excipient is added to obtain a galenic formulation for optimal dispersion in physiological fluids of the digestive tract and food in the digestive tract.

Galenic formulation and the dosage form serve to ensure optimal mixture of the iron-oxide-crystal-based phosphate adsorbent.

The excipient according to the invention (iii) is selected from polymeric carbohydrates.

The pharmaceutical excipient (iii) is preferably selected from glucans such as dextran, starch, cellulose, polymaltose, dextrin, glycogen, pullulan, carboxymethyl cellulose,
fructans such as inulin,
and gum arabic,
or mixtures thereof.

More preferably, the pharmaceutical excipient (iii) is selected from fructans, especially inulin.

Preferred mixtures are mixtures of fructan(s) such as inulin with glucan(s) such as starch and/or carboxymethyl cellulose.

Other preferred mixtures are mixtures of fructan(s) such as inulin with gum arabic, especially inulin with gum arabic.

Examples 1 to 5 show that pharmaceutical preparations with a combination of inulin and gum arabic achieve particularly high phosphate adsorption, as seen from examples 1, 1b, 5a, and 5g. Comparison of phosphate adsorption in examples 1 and 2 clearly shows that the combination of inulin and gum arabic used as a pharmaceutical excipient is especially effective since a higher phosphate adsorption was found in example 1 compared with example 2, where inulin was used alone.

Further Components

The phosphate adsorbent according to the invention preferably can comprise further components, which preferably increase the phosphate binding capacity.

In one embodiment, the further component is ascorbic acid.

In one embodiment, ascorbic acid added to the phosphate adsorbens in final drug formulation for pH adjustment with the property of an enhancement of the total phosphate adsorption capacity, such as it is shown in example 7b. The increase of phosphate binding capacity due to the addition of ascorbic acid is not only related to pH lowering because pH lowering alone using hydrochloric acid as shown in example 7c results in a minor phosphate adsorption compared to example 7b.

In one embodiment, the further component is gelatine.

For example, the final drug application form of the phosphate adsorbent according to the invention comprising gelatine, preferably an aqueous gelatine preparation (such as gelatine with a gel strength between 10 and 300 Bloom gel strength units), is an oral dosage form, preferably in the form of a gel, gel caps or jelly beans. Said final drug application form of the phosphate adsorbent according to the invention results in further increase of the patient compliance, drug tolerance and an enhancement of the phosphate binding capacity, such as shown in example 7d.

Phosphate Binding Capacity

The phosphate adsorbent according to the invention preferably has a phosphate binding capacity of at least 300 mg phosphate per gram of iron, preferably over 500 mg/g of iron.

Figure 2:
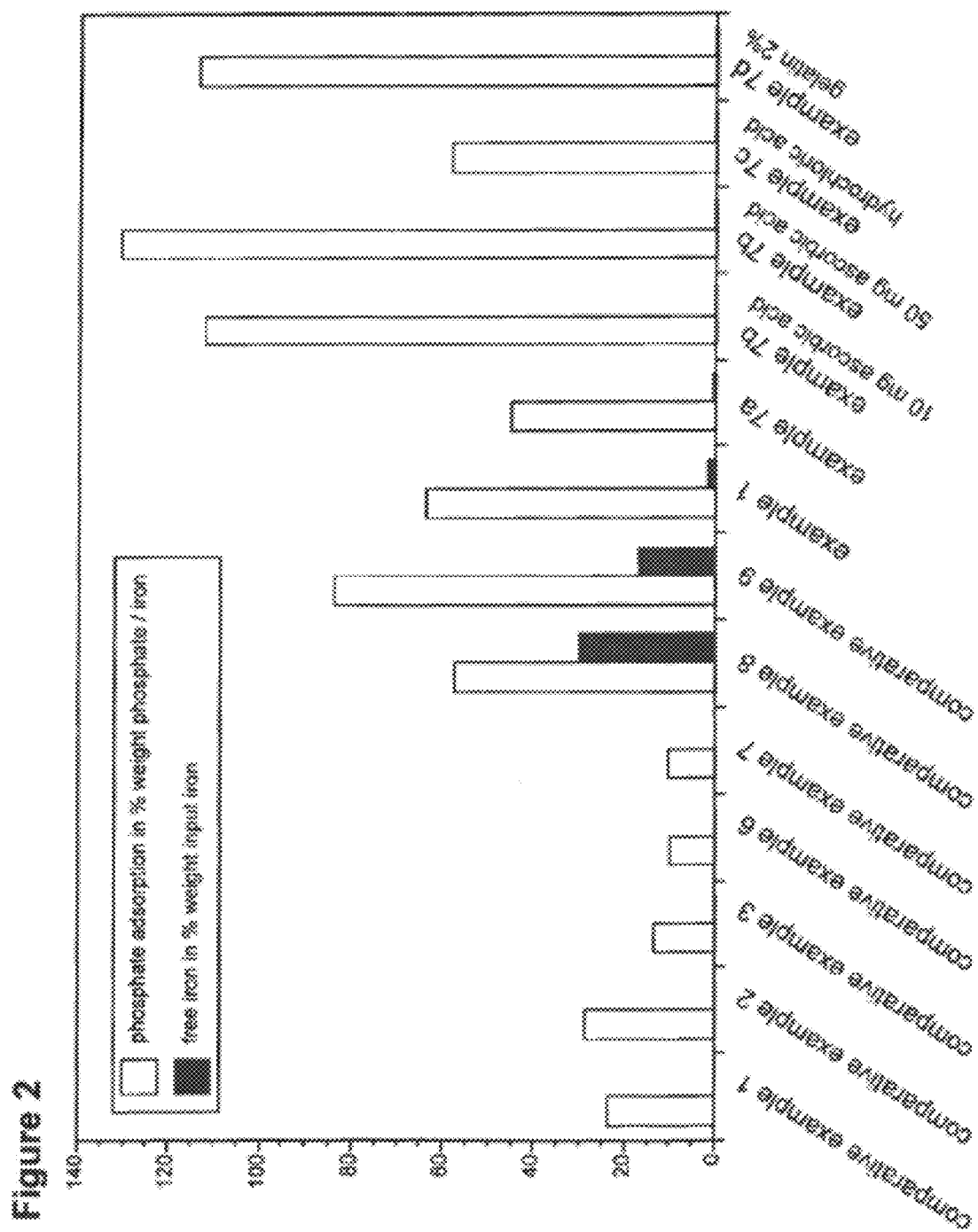

Phosphate adsorbents described in the prior art have a much lower phosphate-binding capacity, such as shown in FIG. 2.

See examples. Example 1 shows adsorption of 640 mg of phosphate per gram of iron in Nutricomp MCT simulated gastrointestinal contents. Comparative example 1 (according to WO 2006/000547 A2, example 3) shows adsorption of 240 mg of phosphate per gram of iron in Nutricomp MCT. Comparative example 2 (according to WO 2008/071747, example 2), showed adsorption of 225 mg of phosphate per gram of iron.

Further example 7a shows an adsorption of 480 mg per gram iron in Nutricomp MCT which is further enhanced by the addition of ascorbic acid to a maximum of 1310 mg bound phosphate per gram iron. A final drug application gel form using gelatin as the pharmaceutical drug vehicle has an adsorption of 1140 mg phosphate per gram iron.

Reduction of Iron Release

The phosphate adsorbent according to the invention preferably has an iron release of less than 10% of the total iron input.

In one embodiment, the phosphate adsorbent according to the invention preferably has an iron release of less than 8%, more preferably less than 5% of the total iron input, such as less than 2% or less than 1% of the total iron input, such as about 1.5% or about 1% or about 0.5%.

Phosphate adsorbents described in the prior art with an phosphate adsorption above 500 mg phosphate per gram iron in Nutricomp MCT, such as described in comparative example 8 (according to U.S. Pat. No. 7,767,851 B2) and 9 show an iron ion release in relation to total iron input of 30.6% and 17% respectively. In contrast to this example 1, 7a-d exhibit an iron ion release less than 2 and 1% respectively.

Method for the Production of the Phosphate Adsorbent

The object is solved according to the invention by a method for producing a phosphate adsorbent.

Production of the Phosphate Adsorbent with (Primary) Coating (ii)

The method according to the invention comprises alkaline precipitation of iron(II) and iron(III) salt solutions with a base in the presence of a carbohydrate matrix, which, according to the invention, is a compound selected from (a) mono- or disaccharides or (b) alditols or mixtures thereof (with the said carbohydrate matrix or compound forming the coating (ii) of the iron oxide cores (i)).

The base is preferably selected from NaOH, KOH, or ammonium hydroxide or mixtures thereof.

The phosphate adsorbent prepared according to the invention is based on maghemite or a mixture of maghemite and magnetite.

Preferably, the iron(II) and iron(III) salt solutions are solutions of iron(II) chloride and iron(IIII) chloride.

Alkaline precipitation is preferably performed at a temperature of 0 to 25° C., preferably 0 to 20° C., more preferably 4 to 12° C.

The iron(II) and iron(III) ions are preferably present in a molar ratio of 0.4 to 0.7, more preferably in a molar ratio of 0.5 to 0.66.

Alkaline precipitation is performed in the presence of a compound selected from (a) mono- or disaccharides or (b) alditols or mixtures thereof.

The aliphatic or cyclic mono- or disaccharides (a) are preferably selected from mono- or disaccharides of aliphatic and/or aromatic hexoses or pentoses, more preferably from mannose, saccharose, fructose, fucose, trehalose, glucose, rhamnose, galactose, maltose, and arabinose, and even more preferably from mannose, maltose, and/or saccharose.

The alditols (b), or sugar alcohols, are preferably selected from mannitol, sorbitol, isomalt, threitol, lactitol, xylitol, arabitol, erythritol, and glycerol, more preferably from mannitol.

In a preferred embodiment, the compound is present in excess (in molar excess in relation to iron), with "in excess" referring to the molar ratio of the compound to the available binding sites on the iron oxide crystal surfaces (of the iron oxide cores (i)).

The iron oxide cores (i) and the coating (ii) are in thermodynamic equilibrium, i.e., bound in complexes and in solution/dispersion. An excess of compound (ii) increases the likelihood of the surfaces of the iron oxide cores being coated; which is advantageous for preventing undesired aggregate formation of iron oxide particles with unsaturated. As outlined above, the coating (ii) (which forms from the compound present during production according to the invention) prevents mutual aggregation of the iron oxide crystals and undesired interactions with components of physiological fluids in the gastrointestinal tract and food contents in the gastrointestinal tract, while at the same time being displaceable by inorganic phosphate.

As also outlined above, the interaction between the iron oxide surface and the compound (ii) may be based on salt formation, van der Waals forces, complex formation, and other electrostatic interactions, and it may be based on covalent bonding. Interactions of the compound (ii) with the iron oxide surfaces result in a thermodynamic equilibrium between free compound in the solution and compound bound to iron oxide surfaces according to chemical and physical laws. In order to ensure adequate coating of the iron oxides by the compound (ii) and to ensure reliable stabilization of the dispersion of iron oxide crystals during production and handling, it is necessary that the compound forming the coating is present in molar excess relative to the potentially available binding sites on the iron oxide surfaces. This is reliably accomplished if, in the production procedure, the compound (ii) is present during the primary crystallization reaction in a ratio of primary coating molecules to total iron of at least 1:1.2 (up to approx. 10-fold excess, preferably 2- to 5-fold molar excess). Better results in terms of phosphate binding are achieved if—as shown in example 1—the molar ratio of primary coating material to total iron during primary crystallization in the production process is for instance is a three fold excess.

As also outlined above, the said molar excess of the compound (ii) is achieved during the production of the phosphate adsorbent according to the invention by: (1) adding the compound/coating (ii) during the crystallization process in a ratio to total iron (sum of ferrous and ferric iron) at a molar excess of at least 1.2 (up to 10-fold excess), preferably 2- to 5-fold molar excess, for example 3-fold excess (see example 1);

(2) optionally adding additional compound/coating (ii) after the purification steps (dialysis, ultrafiltration, centrifugation, diafiltration) in an amount that corresponds to between 5 and 20% of the amount initially used in the primary reaction mixture.

Process Steps

A method according to the invention preferably comprises these steps:

(1) Preparation of an aqueous solution of iron(II) and iron(III) salts, especially iron(II) chloride and iron(III) chloride.

(2) Preparation of an aqueous solution of a compound selected from
(a) (aliphatic or cyclic) mono- or disaccharides (preferably selected from mono- or disaccharides of aliphatic and/or aromatic hexoses or pentoses such as mannose, saccharose, fructose, fucose, trehalose, glucose, rhamnose, galactose, maltose, and arabinose, or
(b) alditols (preferably selected from mannitol, sorbitol, isomalt, threitol, lactitol, xylitol, arabitol, erythritol, and glycerol, more preferably from mannitol), or mixtures thereof.
(3) Combining of solutions (1) and (2) and addition of a base to obtain a suspension with pH of 7 to 13.

The base is preferably selected from NaOH, KOH, or ammonium hydroxide or mixtures thereof.

The temperature is 0 to 25° C., preferably 0 to 20° C., more preferably 4 to 12° C.

The compound in step (2) is preferably selected from mannose, maltose, saccharose, and/or mannitol.

The compound in step (2) is preferably available in excess, as described above.

The compound in step (2) is preferably available in molar excess relative to total iron (sum of ferrous and ferric iron) of at least 1.2 (up to 10-fold excess), preferably 2- to 5-fold molar excess, for example 3-fold excess.

A method according to the invention further preferably comprises step (4):
(4) Oxidation by adding an oxidizing agent and/or introducing air or pure oxygen gas at a temperature between 25° C. and 90° C., preferably 40 and 65° C.

The preferred oxidizing agent is hydrogen peroxide or nitric acid in combination with iron nitrate.

In step (4), magnetite is oxidized to form maghemite. This is an important step, since without this measure, oxidation would occur spontaneously over weeks, with release of reactive iron, which may be toxic or result in an unstable dispersion.

In addition to ensuring optimal phosphate binding, an iron-based phosphate adsorbent must be highly stable to minimize release of iron from the crystals. Magnetite from the group of inverse spinel iron oxides easily oxidizes and hence is less stable. Without controlled oxidation, magnetites would undergo spontaneous oxidation during storage, releasing ferrous and ferric ions, which might cause undesired adverse effects when such a preparation is used in patients. It is therefore necessary and preferred to perform a controlled oxidation and to remove any iron ions released during this reaction. Oxidation can be induced by adding hydrogen peroxide as an oxidizer in aqueous solution or by introducing room air or pure oxygen into the aqueous solution. Iron ions released during oxidation are preferably separated and removed in a further step (see step (5)) using sedimentation of the magnetic dispersion with a magnet or centrifugation and withdrawal of the supernatant. Moreover, these reaction products can be removed by dialysis, ultrafiltration, or diafiltration.

A method according to the invention further preferably comprises step (5):
(5) Removal of unbound iron(II) ions and/or iron(III) ions by centrifugation, dialysis, magnetic separation, and/or ultrafiltration.

A method according to the invention further preferably comprises step (6):
(6) Addition of a pharmaceutical excipient selected from polymeric carbohydrates.

The pharmaceutical excipient (iii) is preferably selected from
glucans, such as dextran, starch, cellulose, polymaltose, dextrin, glycogen, pullulan, carboxymethyl cellulose,
fructans, such as inulin,
and gum arabic,
or mixtures thereof.

More preferably, the pharmaceutical excipient (iii) is selected from fructans, especially inulin.

Preferred mixtures are mixtures of fructan(s), such as inulin, with glucan(s), such as starch and/or carboxymethyl cellulose.

Further preferred mixtures are mixtures of fructan(s), such as inulin, with gum arabic, especially inulin with gum arabic.

The pharmaceutical excipient is added to provide a secondary coating and to ensure pharmaceutical formulation of the phosphate adsorbent according to the invention as described herein. The addition of the excipient primarily enables drying to a fine powder.

The preferred amount of excipient to be added is such that the total iron content of the resulting phosphate adsorbent is between 100 and 300 mg in the dried state.

In one embodiment of the method according to the invention, in step (6) the compound from step (2) (the coating (ii)), is added again, either simultaneously with the excipient or separately.

Thereby, in step (6), the preferred amount of the compound from step (2) (the coating (ii)) to be added is less than 2 weight % of the amount of the compound (ii) initially added according to step (2).

In one embodiment, the method according to the invention comprises a washing step (preferably after step (6)) using the compound from step (2) for washing.

Washing is performed with an aqueous solution of the compound from step (2) at a concentration between 2 and 5% (weight/volume). This washing step serves to remove undesired reaction products after step 6 in order to prevent removal of too large a proportion of stabilizing compounds (ii) or (iii), thereby precluding possible undesired aggregation of the iron oxide crystals.

A method according to the invention further preferably comprises step (7):
(7) Drying of the resulting suspension using lyophilization and/or heat drying.

Production of the Phosphate Adsorbent without (Primary) Coating (ii)

In one embodiment the phosphate adsorbent according to the invention comprises iron oxide cores (i) with a pharmaceutical excipient (iii).

According to the invention, the method for producing this embodiment corresponds to the method described hereinabove except that step (2) is left out and step (3) below is performed instead:
(3) Addition of a base to solution (1) to obtain a suspension with a pH of 7 to 13.

The base is preferably selected from NaOH, KOH, or ammonium hydroxide or mixtures thereof.

As described above, the method according to the invention comprises the following steps
(1) Preparation of an aqueous solution of iron(II) and iron(III) salts
(2) left out,
(3) Addition of a base, selected from NaOH, KOH, or ammonium hydroxide or mixtures thereof, to solution (1) to obtain a suspension with a pH of 7 to 13, at a temperature between 0 to 25° C., preferably 0 to 20° C.

As described above, the method according to the invention further comprises the following step(s):

(4) Oxidation by adding an oxidizing agent and/or introducing air or pure oxygen gas at a temperature between 25° C. and 90° C., preferably between 40 and 65° C. and/or (5) Removal of unbound iron(II) and/or iron(III) ions by centrifugation, dialysis, magnetic separation, and/or ultrafiltration. and/or (6) Addition of a pharmaceutical excipient selected from polymeric carbohydrates,
preferably selected from
glucans such as dextran, starch, cellulose, polymaltose, dextrin, glycogen, pullulan, carboxymethyl cellulose,
fructans such as inulin,
and gum arabic,
or mixtures thereof.
and/or (7) Drying of the resulting suspension using lyophilization and/or heat drying.

According to the invention, the iron oxide cores of the inverse spinel type (i) can also be produced without primary coating (ii) and used as phosphate adsorbent. The phosphate adsorbent prepared in this way (see example 6) has lower phosphate adsorption compared with the same phosphate adsorbent produced with a coating of compound (ii) (as in example 1); however, the phosphate-binding capacity of this uncoated form is higher/better than that of known iron-hydroxide-based phosphate adsorbents (see for instance comparative examples 1 and 2).

Product of the Method

The object is solved according to the invention by providing a phosphate adsorbent obtained by a method according to the invention, as described herein.

The object is solved according to the invention by providing a phosphate adsorbent according to the invention, as described herein, obtained by a method according to the invention, as described herein.

According to the invention, the resulting phosphate adsorbent has the form of nanoparticles.

According to the invention, the nanoparticles have a particle size of the iron oxide core (i) of less than/smaller than 20 nm, preferably less than/smaller than 10 nm.

According to the invention, the nanoparticles have a particle size of the iron oxide core (i) of preferably 2 to 20 nm, more preferably 2 to 5 nm.

According to the invention, the resulting phosphate adsorbent has an iron content which is about
3 to 50 wt-% of total weight of the phosphate adsorbent, such as
3 to 45 wt-% of total weight of the phosphate adsorbent,
5 to 45 wt-% of total weight of the phosphate adsorbent,
10 to 45 wt-% of total weight of the phosphate adsorbent,
15 to 45 wt-% of total weight of the phosphate adsorbent,
3 to 40 wt-% of total weight of the phosphate adsorbent,
5 to 40 wt-% of total weight of the phosphate adsorbent,
10 to 40 wt-% of total weight of the phosphate adsorbent,
15 to 40 wt-% of total weight of the phosphate adsorbent,
3 to 35 wt-% of total weight of the phosphate adsorbent,
5 to 35 wt-% of total weight of the phosphate adsorbent,
10 to 35 wt-% of total weight of the phosphate adsorbent.
15 to 35 wt-% of total weight of the phosphate adsorbent, Pharmaceutical Compositions The object is solved according to the invention by providing a pharmaceutical composition comprising a phosphate adsorbent according to the invention, as described herein.

The object is solved according to the invention by providing a pharmaceutical composition comprising a phosphate adsorbent according to the invention obtained by a method according to the invention, as described herein.

A pharmaceutical composition according to the invention optionally comprises further pharmaceutically active excipient(s), such as silicium oxide, talcum, gelatin, polyethylene glycol, magnesium oxide, magnesium carbonate, chitosan.

A pharmaceutical composition according to the invention optionally comprises one or several further active agent(s) such as iron hydroxide (e.g., hematite, goethite, akaganeite, lepidocrocite), lanthanum carbonate, calcium acetate, magnesium carbonate, or sevelamer.

In one embodiment, a pharmaceutical composition according to the invention comprises ascorbic acid as further active ingredient.

The pharmaceutical excipient (iii) of the phosphate adsorbent is preferably selected from fructans, such as inulin, or is a mixture of fructan, especially inulin, with gum arabic as a galenic formulation.

A pharmaceutical composition according to the invention optionally comprises pharmaceutical vehicle(s) or carrier(s).

In one embodiment, a pharmaceutical composition according to the invention comprises gelatine as a pharmaceutical vehicle.

The gelatine is preferably an aqueous gelatine preparation, preferably gelatine with a gel strength between about 10 and about 300 Bloom gel strength units.

For example, gelatine with a gel strength between about 10 and about 100 Bloom gel strength units, such as for providing a gel dosage form (e.g. sachets); or a gelatine with a gel strength above about 100 Bloom gel strength units, such as about 100 to 300 Bloom gel strength units, such as for drops with different solidity/strength.

Said pharmaceutical composition comprising gelatine is preferably in an oral dosage form preferably in the form of a gel, gel caps or jelly beans.

Using gelatine as the pharmaceutical vehicle the drug substance is predispersed in a final application form and released subsequently in the gut and intestinal content. A final drug application form as gel, gel caps or jelly beans may enhance the patient compliance in daily drug intake. Further the gelatine as the drug vehicle increases further the phosphate adsorption, such as shown in example 7d.

The pharmaceutical composition is preferably available in an oral pharmaceutical form.

An (oral) pharmaceutical form according to the invention is preferably selected from granules, tablets, capsules, pills, lozenges, chewable tablets, chewing gum, fruit gum, powder for solution, solutions, dispersions, suspensions, emulsions, and gels. Gels can be gel caps or jelly beans.

In one embodiment the pharmaceutical composition is available in an oral continuous slow-release composition, i.e., an oral composition that ensures continuous slow release or delayed release.

According to the invention, an oral continuous slow-release composition is a composition that continuously releases the active agent into the gastrointestinal tract including the oral environment (oral cavity, saliva).

This also comprises compositions which continuously release the active agent slowly or in a delayed manner, such as chewing gum—provided they are kept in the mouth long enough.

A pharmaceutical form that remains in the mouth long enough allows adsorption of phosphate from the saliva, which can be accomplished for example by chewable tablets with slow release of the active agent. When the pharmaceutical form is administered as a chewing gum, the active agent can remain within the chewing gum and adsorb phosphate from the saliva, thereby eliminating the phosphate when the chewing gum is taken out of the mouth before it reaches the gastrointestinal tract, and/or the active agent is also slowly released from the chewing gum into the saliva, thereby binding the phosphate to prevent enteral absorption.

A drug or a pharmaceutical composition comprises a therapeutically active amount of the active agent (phosphate adsorbent according to the invention). An expert is able to determine the therapeutically active amount required for treatment based on the disease to be treated and the patient's condition. A suitable single dose of a drug or pharmaceutical composition contains approximately between 0.1 and 1000 mg, preferably approximately 10 to 500 mg, of a phosphate adsorbent according to the invention.

The pharmaceutical compositions according to the invention are further characterized in that the active agent (phosphate adsorbent according to the invention) is present in an amount resulting in a concentration range of preferably 0.1 to 100 mM, more preferably 1 to 10 mM in the digestive tract or in biological fluids, when used for in vivo treatment.

In one embodiment, the pharmaceutical composition is available in a pharmaceutical form for parenteral administration, especially intravenous administration.

As described hereinabove, mixtures of aliphatic or cyclic mono- or disaccharides with mannitol are especially preferred for coating (ii) when a pharmaceutical composition for parenteral (especially intravenous) administration is prepared.

Drops in serum phosphate levels are known adverse effects of iron preparations used for intravenous treatment of anemia.

The phosphate adsorbent according to the invention, when provided in a pharmaceutical form for parenteral, especially intravenous administration, is suitable for short-term reduction of the serum phosphate level in severe imbalance after IV treatment with said iron preparations.

See example 7. Example 7 shows phosphate adsorption in serum comparing the phosphate adsorbent according to the invention (from example 1) with a commercially available drug on the basis of inverse spinel iron oxide (with larger particles compared with particle size according to the invention) with a (strongly) stabilizing coating of carboxymethyl dextran (Feraheme®). Feraheme® shows very much lower phosphate adsorption in serum than the phosphate adsorbent according to the invention (from example 1). Here, the phosphate adsorbent according to the invention (from example 1) is a stable aqueous dispersion allowing parenteral, particularly intravenous administration.

Medical Uses

The object is solved according to the invention by providing the phosphate adsorbent according to the invention or the pharmaceutical composition according to the invention for use as a pharmaceutical.

The object is solved according to the invention by providing the phosphate adsorbent according to the invention or the pharmaceutical composition according to the invention for use in the prevention and/or treatment of hyperphosphatemia.

A "phosphate adsorbent according to the invention" refers to a phosphate adsorbent as described herein and to a phosphate adsorbent obtained by a method according to the invention as described herein.

The phosphate adsorbent according to the invention or the pharmaceutical composition according to the invention is preferable available in a dosage form/formulation (suitable) for oral and/or intravenous administration.

In one embodiment, the phosphate adsorbent according to the invention or the pharmaceutical composition according to the invention is provided for
selective removal or elimination of inorganic phosphate from fluids such as hemodialysis fluids, whole blood, or plasma, or from foods,
lowering of serum phosphate levels,
removal of phosphate from saliva,
maintaining a physiological (serum) phosphate level
in a subject in need of such treatment. These are patients with impaired renal function/chronic renal disease without or with need for hemodialysis.

The use of phosphate binders on the basis of iron oxide crystals has several advantages for patients with impaired renal function. Medications on the basis of iron for treating hyperphospatemia can be manufactured at low cost, and adverse events are not likely to occur. Patients on hemodialysis generally require iron replacement therapy since considerable amounts of iron are eliminated by hemodialysis treatment. Hence, potential gastrointestinal absorption of small amounts of iron is not an undesired adverse effect. On the contrary, it even has a therapeutic benefit in this patient population compared with the undesired risks associated with aluminium, calcium, or lanthanide from other phosphate binders.

In one embodiment, the phosphate adsorbent according to the invention or the pharmaceutical composition according to the invention is provided for
short-term lowering of the phosphate serum level,
in particular via parenteral administration, more particularly intravenous administration.

In one embodiment, the phosphate adsorbent according to the invention or the pharmaceutical composition according to the invention is provided for the treatment of humans and/or animals.

Formulations with Fructans as Pharmaceutical Excipient (iii)

The present invention further provides pharmaceutical compositions comprising an active agent and a pharmaceutical excipient selected from fructans, such as inulin, and gum arabic or mixtures thereof, and optionally one or several further pharmaceutical excipients.

The pharmaceutical compositions preferably comprise a mixture of fructan (especially inulin) and gum arabic.

Preferred are galenic formulations.

DETAILED DESCRIPTION OF THE INVENTION

The essence of the present invention is a phosphate adsorbent and the production thereof for the treatment of elevated serum phosphate levels with the phosphate adsorbent being based on inverse spinel iron oxide nanocrystals, which irreversibly bind phosphate in the gastrointestinal tract, thereby ensuring safe elimination of the phosphate. The essence of the invention further includes the production of a pharmaceutical drug for oral administration with an active agent consisting of inverse spinel iron oxide nanocrystals in a suitable pharmaceutical formulation and dosage form.

The essence of the invention further lies in that the inverse spinel iron oxide core of the novel phosphate adsorbent consists of maghemite (gamma-$Fe_2O_3$) with a magnetite component ($Fe_3O_4$) defined by a proportion of ferrous ions ideally of less than 20% and contains less than 20% non-inverse spinel iron oxides (expressing the proportion of ferrous iron in relation to total iron as a molar ratio is equivalent to giving the percentage weight since ferrous iron has one electron more than ferric iron, which is negligible relative to total mass). The embodiment of the invention further includes that the active agent of the phosphate adsorbent consists of monocrystalline inverse spinel iron oxide with crystallite sizes of less than 20 nm, preferably 2 to 20 nm, more preferably between 2 and 5 nm. Initial crystallization in aqueous alkaline solution occurs in the presence of aliphatic and/or cyclic mono- and/or disaccharides (e.g., frucose, mannose) and/or alditols (e.g., mannitol, sorbitol), which is necessary to preferably obtain monocrystalline iron oxides of the inverse spinel type.

The essence of the invention further lies in that the phosphate adsorbent has an iron content which is about 3 to 50 wt-% of total weight of the phosphate adsorbent. This iron content complies with the different requirements or needs of a phosphate adsorbent. On one hand, there is a need for a minimum of stabilizing excipients resulting in an optimal storage stability, release of the iron surface for phosphate adsorption, prevention of agglomeration in the intestinal tract and prevention of iron related toxicity in biological systems. On the other there is need for a reduction of pill burden and it is not of benefit according this clinical topic to minimize the content of the active ingredient (i.e. iron content) below about 3% of the total adsorbent drug.

Another embodiment of the invention is the need for controlled oxidation of the initially produced magnetites by adding oxidizers and/or introducing room air or pure oxygen gas during heat application in order to keep the proportion of ferrous ions below 20% (weight/weight total iron). The principle of phosphate adsorption in the body in vivo from biological fluids or fluids in the gastrointestinal tract and the entire contents of the gastrointestinal tract is based on the displacement of the primary coating, which is necessary for stabilization, by phosphate. The primary coating ensures temporary stabilization of the inverse spinel iron oxide crystals in the aforementioned fluids in order to maximize the adsorptive surface area, which is at least 200 m² per gram of iron. (At a density of a maghemite with a small magnetite proportion of 5 g/cm³, a surface area of 233 m² per gram of total iron is calculated for a crystal diameter of 10 nm. Correspondingly, the total surface area per gram of iron increases to 560 m² for a crystal diameter of 3 nm).

The very small iron oxide crystals of the inverse spinel type according to the invention for use as phosphate adsorbent in the treatment of abnormally elevated phosphate serum levels are obtained from ferric iron salts and ferrous iron salts by a precipitation reaction in aqueous medium induced by addition of a base in the presence of monomeric or dimeric coating material. This precipitation leads to the formation of magnetite crystals. By additional oxidation, the magnetite crystals become maghemite crystals. In contrast to this procedure, the iron oxides of WO 2006/000547 A2 and WO 2008/071747A1 and U.S. Pat. No. 7,767,851 B2 are exclusively produced from ferric iron chloride, which leads to the formation of iron hydroxides or iron oxy-hydroxides but not to the formation of magnetite or maghemite.

The formation of iron oxides of the inverse spinel type requires ferrous ions in a close reaction with ferric ions. A reaction of ferrous iron alone through alkalization does not yield inverse spinel iron oxide. The same holds true for the reaction of ferric iron alone with addition of a base. When the molar ratio of ferric iron to ferrous iron is below 0.4 or above 0.7, other iron oxides will form in addition to magnetite or maghemite.

An embodiment of the present invention is the production of a nanoparticle dispersion from inverse spinel iron oxide in an aqueous alkaline precipitation in the presence of carbohydrates of the mono- and disaccharides and/or alditols as reaction matrix and primary coating material to obtain crystallite sizes of less than 20 nm, preferably 2-20 nm, and more preferably 2-5 nm. The very small and stable iron oxides provide a large surface area for the adsorption of phosphate in the treatment of high phosphate levels in patients with impaired renal function.

Surprisingly, it was found that the inverse spinel iron oxide crystals produced in this way have very much higher phosphate adsorption (examples 1, 2, 3) than other known phosphate binders on the basis of iron hydroxide (comparative examples 1 and 2).

An embodiment of the invention presented here is a phosphate adsorbent on the basis of spinel iron oxide that is produced by alkalization of a mixture of ferrous and ferric iron. The preferred base for alkalization of the initial reaction mixture is sodium hydroxide. KOH can also be used. Ammonium hydroxide can also be used for this purpose (as shown in comparative example 3). However, this would require careful removal of ammonium ions, which are toxic for mammals.

Another embodiment of the invention is the production of the phosphate adsorbent on the basis of inverse spinel iron oxide under cooling conditions. This is clear from the comparison of example 1 and example 1B, which differ in that production occurs under cooling in example 1. Phosphate adsorption of example 1 is higher than that of example 1B. Nevertheless, example 1B still has higher phosphate adsorption than other known (and patented) iron-oxide-based phosphate adsorbents (comparative examples 1 and 2).

Another embodiment of the invention is the presence of a carbohydrate matrix during formation of the iron oxide crystals. Ideally, the sugar matrix consists of mono- and/or disaccharides such as mannose, saccharose, trehalose, glucose, rhamnose, galactose, and/or alditols such as mannitol or sorbitol. This sugar matrix forms a coating around the crystals forming during crystallization, preventing their aggregation in aqueous dispersions. Nevertheless, this coating can be displaced by phosphate. This becomes clear by the low phosphate adsorption in comparative examples 3 and 4. In comparative example 3, the citrate molecules form strong bonds with the iron oxide surface via two complexing carboxyl groups, and the citrate molecules are replaced with phosphate in very small quantities only, as demonstrated by the low phosphate binding (comparative example 3). Similar in comparative example 4, where the carboxyl groups of the carboxydextran coating undergo a strong interaction with the iron oxide core. This example illustrates that phosphate adsorption is too low if bonding of the coating with the core is too strong. The iron oxide crystal surface coating using carboxy-dextran as the coating material prevents as well replacement of the coating material by phosphate ions as shown in the comparative examples 4 with the commercially available magnetite-maghemite substances Feraheme® and Resovist®.

Another embodiment of the invention is the addition of suitable excipients, which allow drying of the product to a fine powder and ensure optimal mixture with fluids and other contents of the gastrointestinal tract. Examples 1-5 show that the pharmaceutical preparations with the combination of inulin and gum arabic have especially high phosphate adsorption, as shown in examples 1, 1b, 5a, and 5g. Comparison of phosphate adsorption in examples 1 and 2 shows that the combination of inulin and gum arabic as the pharmaceutical excipient is especially effective since phosphate adsorption was found to be lower in example 2, where inulin was used alone, compared with example 1.

Another embodiment of the invention is an increased ratio of phosphate adsorption in relation to release of free iron ions. Iron chelates or iron salt like iron(III) citrate or iron(III) chloride are highly efficacious phosphate adsorbers. Comparative examples 8 and 9 demonstrate high phosphate adsorption but as well the release of free iron ions above 10% of the iron input. In contrast to this obtained iron ion release from iron citrate chelates the crystalline iron hydroxides (comparative example 1 and 2) show only minimal iron release but with a much lower phosphate adsorption. The magnetite-maghemite iron oxide crystal yield sufficient stability against iron release with a high iron bind capacity at the same time (example 1).

Another embodiment of the invention is the addition of further components, such as ascorbic acid.

Another embodiment of the invention is the increase of the phosphate adsorption by the addition of mild acidifying agent with reductive dissolution effect on the iron oxide core and great biocompatibility, like ascorbic acid. As is it shown in comparison of example 7A, 7B and 7C. The addition of ascorbic acid dramatically increased the phosphate adsorption with only minor increase of free iron ion release, which is still far below the iron(III) citrate chelate. On the other hand acidification using hydrochloric acid has no influence on the release of free iron ions but the increase in phosphate adsorption is not as high as with ascorbic acid leading to the conclusion, that a mild reductive dissolution of the iron oxide core with ascorbic acid is more effective in augmentation of the phosphate binding properties of the herein synthesized magnetite-maghemite nanoparticles.

Another embodiment of the invention is the use of aqueous gelatine gel with a Bloom gel strength between 10 and 300. Using gelatine as the vehicle the drug substance is predispersed in a final application form and released subsequently in the gut and intestinal content. A final drug application form as gel caps or jelly beans may enhance the patient compliance in daily drug intake. Further the gelatine gel as the drug vehicle increases further the phosphate adsorption as shown in example 7d.

Another essence of the invention is the option of producing iron oxide crystals of the inverse spinel type without primary coating (ii). The phosphate adsorbent prepared in this way (see example 6) has a lower phosphate adsorption compared with the same phosphate adsorbent produced with a coating of compound (ii); however, the phosphate binding capacity of this uncoated form is higher than that of known iron-hydroxide-based phosphate adsorbents (see comparative examples 1 and 2).

In addition to ensuring optimal phosphate binding, an iron-based phosphate adsorbent must be highly stable to minimize release of iron from the crystals. Magnetite from the group of inverse spinel iron oxides easily oxidizes and hence is less stable. Without controlled oxidation, magnetites would undergo spontaneous oxidation during storage, releasing ferrous and ferric ions, which might cause undesired adverse effects when such a preparation is used in patients. It is therefore necessary and preferred to perform a controlled oxidation and to remove any iron ions released during this reaction. Oxidation can be induced by adding hydrogen peroxide as an oxidizer in aqueous solution or by introducing room air or pure oxygen into the aqueous solution. Iron ions released during oxidation are preferably separated and removed in a further step (see step (5)) using sedimentation of the magnetic dispersion with a magnet or centrifugation and the withdrawal of the supernatant. Moreover, these reaction products can be removed by dialysis, ultrafiltration, or diafiltration.

As discussed above, iron(III) ions can be a basis for metal-based phosphate adsorbers, such as in form of iron (III) citrate having a high phosphorus binding capacity. The production and the use of a pharmaceutical grade iron(III) citrate as an oral phosphate binding drug to treat elevated serum phosphate levels has been laid down by Kwok et al. in U.S. Pat. No. 7,767,851 B2. However, a major drawback of such highly soluble iron salts or chelates, such as iron(III) citrate, is the release of free iron ions, as can be seen in Comparative examples 8 and 9, eading biochemically to oxidative stress with a high risk of iron toxicity. Additionally in patients treated against hyperphosphatemia nearly a life long there is the risk of systemic iron overload due to intestinal iron resorption of the free iron ions, which has been shown for iron(III) citrate (Heinrich, 1987). This results in a limited risk to benefit ratio for these type of iron compounds as phosphate adsorbers.

In contrast thereto, the phosphate adsorbents of this invention do not exhibit such a disadvantageous release of free iron (see also Examples) which renders them suitable for use in the treatment of hyperphosphatemia, also over long periods of time.

Pure magnetite has 30% ferrous ions expressed in relation to total iron (molar ratio). (Expressing the proportion of ferrous iron in relation to total iron as a molar ratio is equivalent to giving the percentage weight since ferrous iron has one electron more than ferric iron, which is negligible relative to total mass.) Another essence of the invention is a phosphate adsorbent on the basis of inverse spinel iron oxide with a proportion of ferrous iron oxides of less than 20%, preferably less than 15%, more preferably less than 10%, and even more preferably less than 5% or less than 3% of the total iron.

The present invention is illustrated in more detail in the following figures and examples, but the invention is not limited thereto. The references are herewith incorporated by reference herein. The figures show:

FIG. 1. Transmission electron microscopy (TEM) images of the production examples (A), (C) Example 1 (B), (D) Comparative example 3 The TEM image of example 1 (A) depicts the extremely small crystals as slightly electron-dense clouds. The individual crystals are too small for the resolution used here. There are only some accumulations of slightly larger crystals, of which only very small amounts are formed using this production procedure. In comparison, the TEM image of a sample produced according to comparative example 3 (B) depicts markedly larger crystals and no clouds of very small crystals. The electron diffraction patterns of example 1 (C) weakly but definitely correspond to the typical patterns of magnetite and maghemite. The electron diffraction pattern is very obvious for the sample of comparative example 3 due to the larger crystals and is also consistent with the typical patterns of magnetite and maghemite.

FIG. 2. Phosphate adsorption and iron release of phosphate adsorbents of the invention compared to phosphate adsorbents of the prior art.

Figure 3:
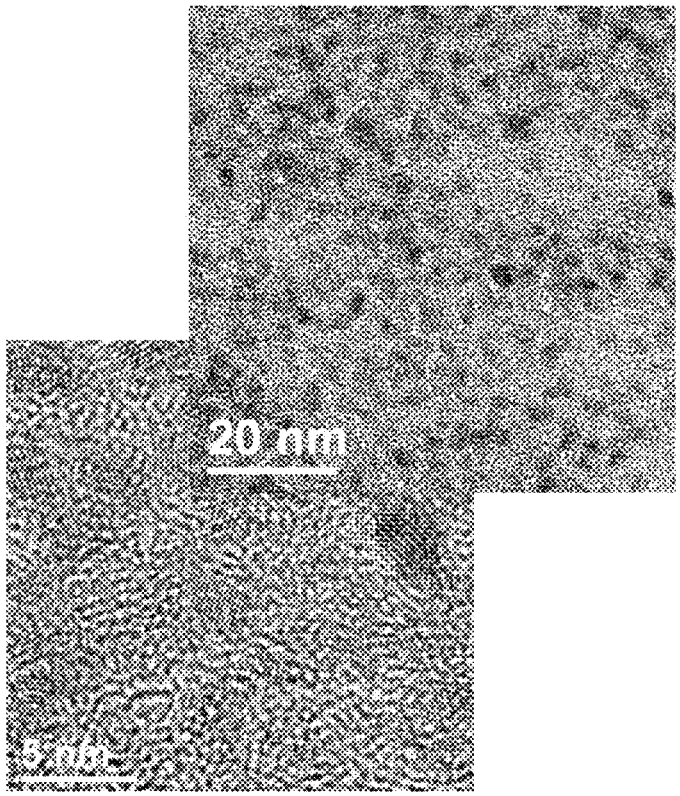
Figure 3:
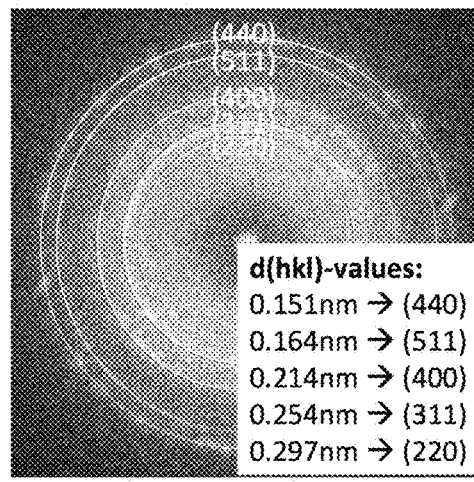

FIG. 3: TEM characterization of the batch used for in-vivo experiments.

Figure 4:
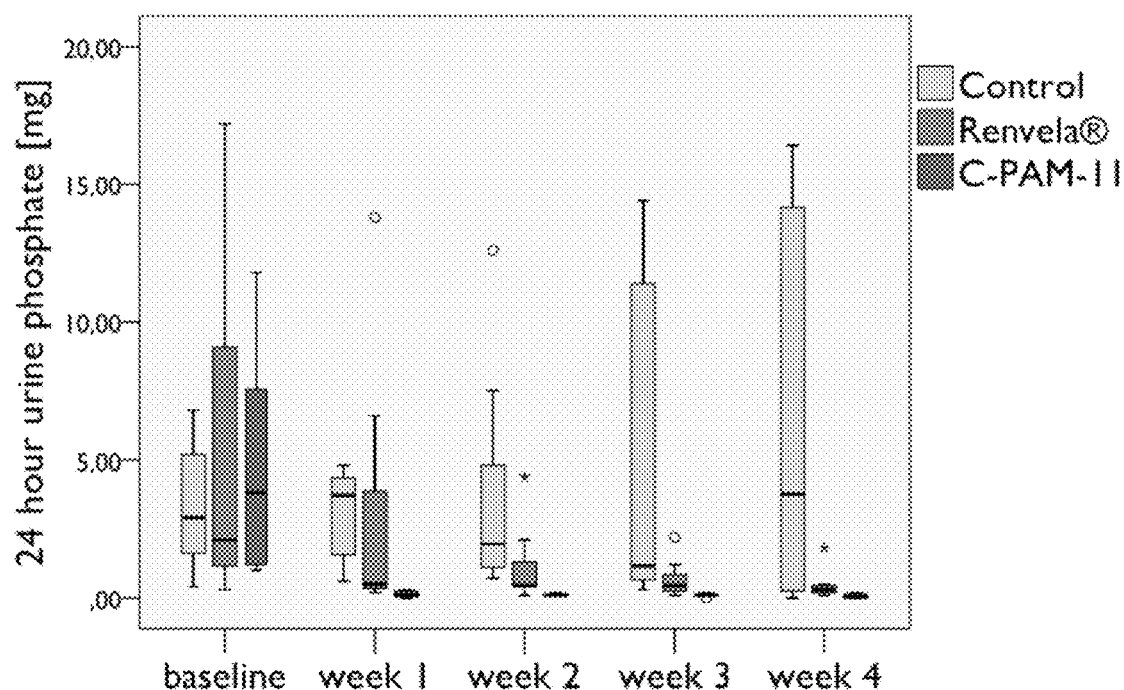

FIG. 4: Urine phosphate excretion expressed in milligram per 24 hours. Due to an intestinal phosphate adsorption by the drug substances the absorption of phosphate in the intestinal brush border was reduced. This results in a reduced urine phosphorus excretion for the group B with Renvela® and more pronounced for the group C with C-PAM-11.

Figure 5:
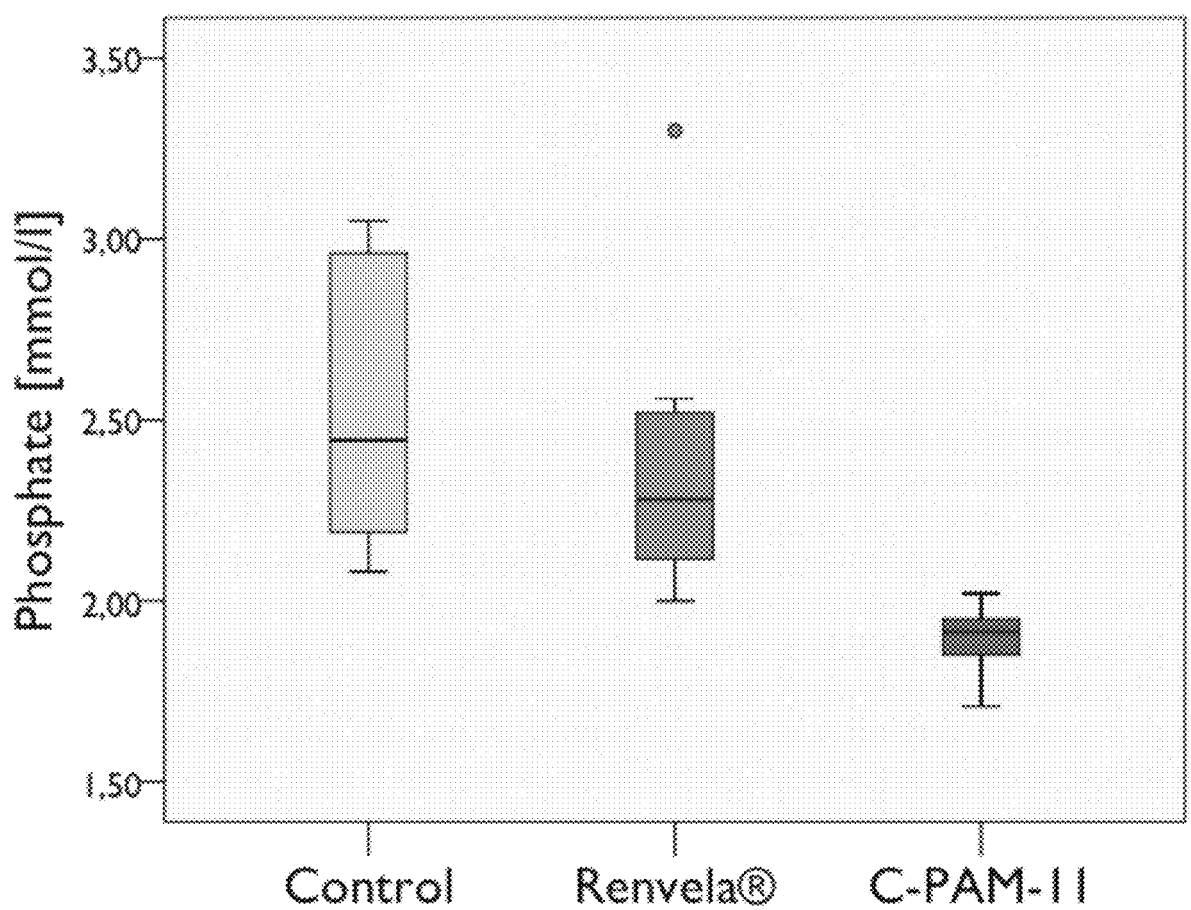

FIG. 5: Serum phosphate level at the 4 week treatment time point. The physiological range for rats is 2.26-3.06 mmol phosphate/l (data provided by breeder Charles River). The rats treated with C-PAM-11 developed a serious hypophosphatemia indicating the intestinal phosphate adsorbing efficacy of the maghemite nanoparticles. This adverse reaction cloud simply be prevented by a further dose reduction.

Figure 6:
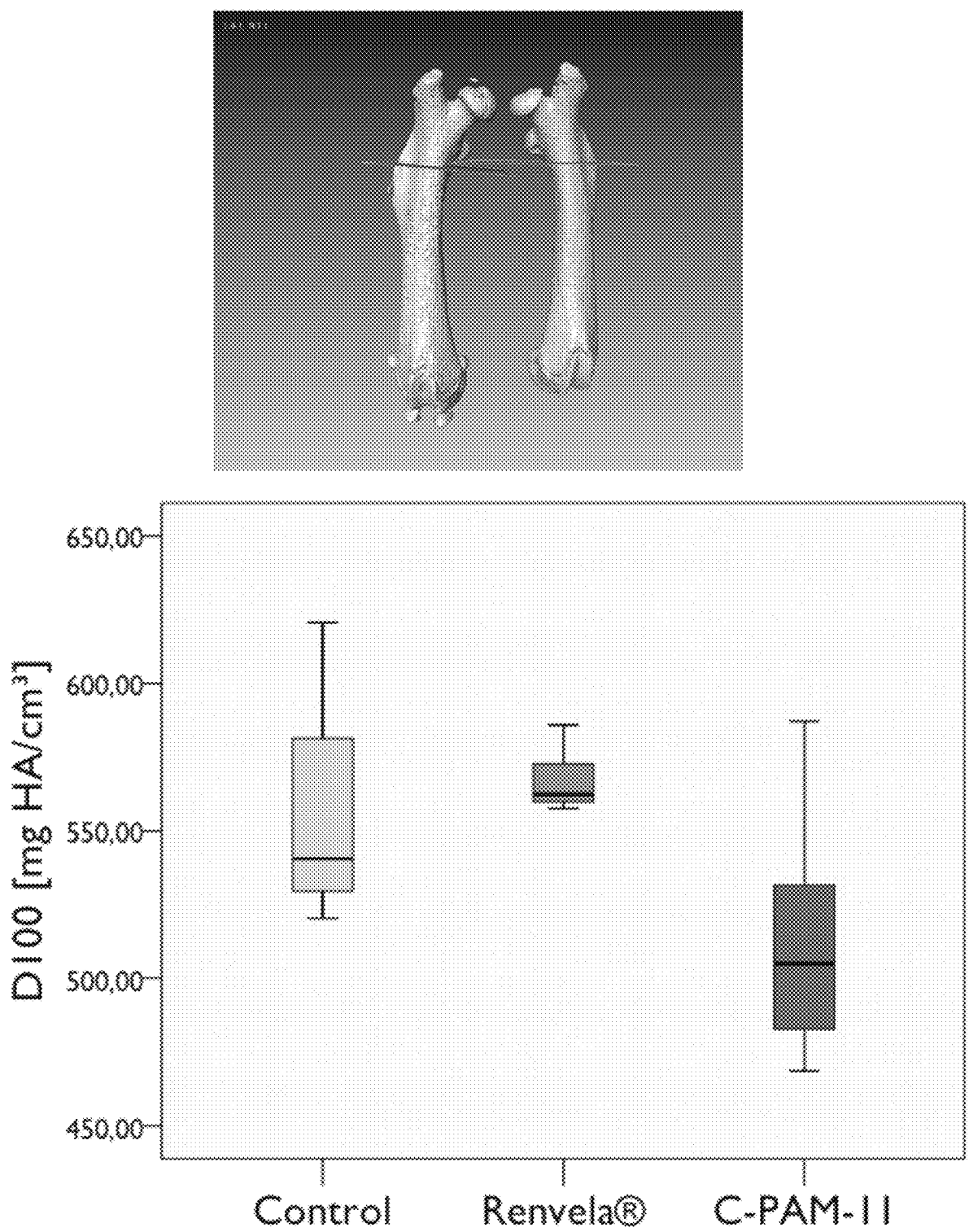

FIG. 6: Left image: High resolution CT of rat femora from the control group (left) and from the C-PAM-11 group (right) group. Graph: Quantitatively measured bone density of rat femora. Bone density was significantly reduced for the C-PAM-11 group as a result of the tremendous serum phosphate lowering efficacy in these healthy rats. This unwanted adverse effect can simply be prevented by a further dose reduction.

EXAMPLES

Analytical Methods and Determination of In Vitro Phosphate Binding

Determination of Phosphate-binding Capacity in Aqueous Solution

Phosphate adsorption was determined in aqueous sodium phosphate solution at pHs of 3, 5.5, and 8. A 40 mM phosphate solution (solution A) was prepared using sodium dihydrogen phosphate (S0751, Sigma-Aldrich, Munich, Germany). The pH was adjusted by adding either sodium hydroxide or hydrochloric acid.

Using solution A as aqueous medium, we prepared solutions of the iron-based phosphate adsorbents, at 0.1 M concentration relative to iron, obtained according to the production examples and comparative examples presented hereinafter (solution B). A 10-ml aliquot of solution B was gently shaken in a waterbath for two hours at 37°. Following incubation, the samples were centrifuged for 10 min (RCF: 2700). The supernatant was filtered again with a 30 kD ultracentrifuge filter. The phosphate content of the filtrate was determined by HPLC (ICS-3000, Dionex) with a IonPac AS14A 4×250 mm column at a flow rate of 1 ml/min using 8 mM sodium carbonate/1 mM sodium hydrogen carbonate as eluent and an injection volume of 0.02 ml.

Determination of Phosphate-Binding Capacity in Simulated Gastrointestinal Contents Nutricomp MCT (B. Braun, Melsungen, Germany) was used as a standardized food suspension to simulate gastric contents. According to the manufacturer, 100 ml of this food suspension contains 86.6 mg phosphorus. During normal digestion, most of the phosphate ingested with the food is released from organic phosphate compounds by alkaline phosphatases and enterally absorbed in the duodenum. It is therefore of foremost importance for a suitable phosphate adsorbent to bind enough of the released phosphate at pHs of over 7. To simulate this gastrointestinal tract environment, the Nutricomp MCT suspension used in these experiments was alkalized with sodium carbonate. The pH of Nutricomp MCT was adjusted to 7.54 by adding 1 M sodium carbonate solution (Natrium Carbonat Decahydrat, Sigma-Aldrich No. 71538). Nutricomp MCT contains phosphorus in the form of organic phosphate compounds. For the experiments described hereinafter, we did not add alkaline phosphatases to release the phosphate from these compounds but instead supplemented Nutricomp MCT with phosphate. A 400 ml sample of Nutricomp MCT solution was supplemented with 1.62 g of sodium dihydrogen phosphate (S0751, Sigma-Aldrich, Munich, Germany) dissolved in 6 ml of 0.9% sodium chloride solution. For pH adjustment, 14 ml of 1 M sodium carbonate solution was added (Sigma-Aldrich, No. 71538). The resulting mixture is hereinafter referred to as food suspension A. The iron-based phosphate adsorbents were added to 15-ml aliquots of food suspension A according to the production and comparative examples presented hereinafter. The amount added resulted in a 0.1 M iron concentration (incubation mixture B). A 10-ml aliquot of said incubation mixture B was shaken in a waterbath for 2 hours at 37° C. Following this incubation period, incubation mixture B was centrifuged (RCF 2700). The supernatant was again filtered with an ultracentrifuge filter with a 30 kD separation membrane. The phosphate content of the filtrate was determined by HPLC (ICS-3000, Dionex) with a IonPac AS14A 4×250 mm column at a flow rate of 1 ml/min using 8 mM sodium carbonate/1 mM sodium hydrogen carbonate as eluent and an injection volume of 0.02 ml.

Determination of Free Iron Ions During Phosphate Adsorption Test

Total iron content in the phosphate adsorption test filtrate was determined by reduction of all iron ions to ferrous iron using the hydroxylamine hydrochloride reagent. Colored ferrous orthophenantroline complex was measured at 510 nm absorbance on a Thermoscientific Genesys 6 spectrophotometer.

Comparative Example 1

An iron-hydroxide-based phosphate adsorbent was prepared according to production example 3 of WO 2006/000547 A2. This method describes the production of an iron-based phosphate adsorbent with optimized phosphate binding.

A solution of 52 g sodium carbonate decahydrate (Sigma-Aldrich, No. 71538) in 78 g bidistilled water was prepared (solution 1). A second solution of 38 g iron(III) nitrate nonahydrate (Sigma-Aldrich, No. 31233) in 16 g bidistilled water was prepared (solution 2). Solution 2 was added dropwise to solution 1 with strong stirring over 30 min. The resulting solution (solution 3) was continued to stir for another 60 min at room temperature and then dialsysed against water in a dialysis tube (Spectra Por dialysis tube, RC membrane, 12-14 kD cutoff). This procedure was continued until, after repeated exchange of water, conductivity in the filtered solution was <0.5 mS/cm. A 100-ml aliquot was taken from the retentate, to which were added 6 g cornstarch (Sigma-Aldrich, No. S 4126) and 6 g sucrose (Sigma-Aldrich, No. S 7903). The red-brown turbit dispersion was reduced to 60 ml at 60° C. on a rotation vaporizer and dried overnight at 60° C. in a cabinet dryer. The resulting red-brown powder was ground to a fine powder with a mortar and pestle. The final powder has an iron content of 276 mg/g.

| Comparative example 1: Phosphate adsorption in aqueous solution at different pHs. | | | | | |
|---|---|---|---|---|---|
| pH | $PO_4$ mg/l | $PO_4$ mg/l filtrate | $PO_4$ mg/l adsorbed | $PO_4$ % adsorbed | $PO_4$ %/Fe (m/m Fe) adsorbed |
| 3 | 4109 | 2667 | 1442 | 35.1 | 25.85 |
| 5.5 | 3990 | 2735 | 1254 | 31.43 | 22.45 |
| 8 | 3985 | 3201 | 784 | 19.67 | 14.04 |

For all experiments, the iron content of the test solution was adjusted to 0.1M.

| Comparative example 1: Phosphate adsorption in Nutricomp MCT. | | | | | |
|---|---|---|---|---|---|
| pH | $PO_4$ mg/l control | $PO_4$ mg/l filtrate | $PO_4$ mg/l adsorbed | $PO_4$ % adsorbed | $PO_4$ %/Fe (m/m Fe) adsorbed |
| 7.54 | 6870 | 5611 | 1259 | 18.3 | 22.52 |
| absolute free iron in filtrate as % of absolute iron input weight | | | | | 0.01 |

For all experiments, the iron content of the test solution was adjusted to 0.1M.

Comparative Example 2

An iron-hydroxide-based phosphate adsorbent was prepared according to production example 2 of WO 2008/071747.

A solution of 15 g sodium carbonate decahydrate (Sigma-Aldrich, No. 71538) in 50 g bidistilled water was prepared (solution 1). A second solution of 13.5 g iron(III) chloride hexahydrate (Sigma-Aldrich, No. 31232) in 22.5 g bidistilled water was prepared (solution 2). Suspension 3 was prepared by adding 3.68 g potato starch (Sigma-Aldrich, No. S 5241) to 20 g bidistilled water. Solutions 1 and 2 were combined with strong stifling by continuously and simultaneously transferring the two solutions into a reaction vessel at a flow rate of 2 ml/min at room temperature. The resulting red-brown turbid suspension was stirred for another hour at 25° C. and then filtered through a grade 595 paper filter (Schleicher-Schüll). The filter retentate was resuspended by washing the filter in 90 g bidistilled water. This filtration and resuspension were repeated twice. The suspension was then filtered once again, and the red-brown dry retentate was detached from the filter and resuspended in 7.5 g bidistilled water, 3.7 g sucrose, and 12 g ethanol (purest quality) and stirred at room temperature for 1 hour. The resulting suspension was reduced to 10 ml on a rotation vaporizer and dried overnight at 60° C. in a cabinet dryer. The fine powder obtained by grinding with a mortar and pestle has an iron content of 186 mg/g dry substance.

| Comparative example 2: Phosphate adsorption in aqueous solution at different pHs. | | | | | |
|---|---|---|---|---|---|
| pH | $PO_4$ mg/l | $PO_4$ mg/l filtrate | $PO_4$ mg/l adsorbed | $PO_4$ % adsorbed | $PO_4$ %/Fe (m/m Fe) adsorbed |
| 3 | 4109 | 2667 | 1627 | 39.6 | 29.13 |
| 5.5 | 3990 | 2473 | 1517 | 38.02 | 27.16 |
| 8 | 3985 | 2797 | 1188 | 29.81 | 21.27 |

For all experiments, the iron content of the test solution was adjusted to 0.1M.

| Comparative example 2: Phosphate adsorption in Nutricomp MCT. | | | | | |
|---|---|---|---|---|---|
| pH | $PO_4$ mg/l control | $PO_4$ mg/l filtrate | $PO_4$ mg/l adsorbed | $PO_4$ % adsorbed | $PO_4$ %/Fe (m/m Fe) adsorbed |
| 7.54 | 6870 | 5516 | 1354 | 19.7 | 23.98 |
| absolute free iron in filtrate as % of absolute iron input weight | | | | | 0.121 |

For all experiments, the iron content of the test solution was adjusted to 0.1M.

Comparative Example 3

A dispersion of inverse spinel iron oxide with a complexing coating of citric acid was prepared according to the publication of Sahoo (Sahoo et al. 2005).

A solution of 1.72 g iron(II) chloride tetrahydrate (Sigma-Aldrich, No. 44939) in 40 ml deoxygenated bidistilled water was prepared (solution A). A second solution of 4.7 g iron(III) chloride hexahydrate (Sigma-Aldrich, No. 31232) in 40 ml deoxygenated bidistilled water was prepared (solution B). Solutions A and B were combined in an argone atmosphere and heated, while stirring, to 80° C. (solution C). At this temperature, solution C was rapidly supplemented with 10 ml of 28% ammonium hydroxide solution in an argone atmosphere (solution D). Solution D was stirred at 80° C. in argone atmosphere for 30 min, to which was then rapidly added 2 g of citric acid (Sigma-Aldrich, No. 251275) dissolved in 4 ml of bidistilled water. The resulting black-brown suspension was stirred in an open vessel with free access to room air for another 90 min at 95° C. After cooling to room temperature, the dispersion was separated on a magnet (1 Tesla) and the supernatant dialysed against 3 l of bidistilled water in a dialysis tube (Spectra Por dialysis tube, RC membrane, 12-14 kD cutoff). The water was exchanged until conductivity in the filtrate was <0.5 mS/cm. The resulting dispersion was reduced to 30 ml on a rotation vaporizer and then supplemented with 3 g inulin and stirred for another 30 min at room temperature. The resulting suspension was dried overnight at 60° C. The dry substance was ground to a fine powder with a mortar and pestle.

The final powder has an iron content of 376 mg/g dry substance and a proportion of ferrous iron of 3.76% in relation to total iron.

| Comparative example 3: Phosphate adsorption in Nutricomp MCT. | | | | | |
|---|---|---|---|---|---|
| pH | $PO_4$ mg/l control | $PO_4$ mg/l filtrate | $PO_4$ mg/l adsorbed | $PO_4$ % adsorbed | $PO_4$ %/Fe (m/m Fe) adsorbed |
| 7.54 | 6870 | 6118 | 752 | 10.95 | 13.48 |
| absolute free iron in filtrate as % of absolute iron input weight | | | | | 0.01 |

For all experiments, the iron content of the test solution was adjusted to 0.1M.

Comparative Example 4

Commercially available colloid dispersions (Resovist®, Feraheme®) of nanoscale magnetite-maghemite iron oxide crystals with modified dextran coating were tested for their phosphate-binding capacity in a phosphate solution at pH 8. Feraheme® has a carboxymethyl dextran coat and is available in a 0.54 M solution relative to iron. Resovist® has a carboxydextran coat and is available in a 0.5 M solution relative to iron. Binding experiments were performed using incubation concentrations corresponding to those of the experiments described above.

| Comparative example Feraheme ®: Phosphate adsorption in aqueous solution at pH 8. | | | | | |
|---|---|---|---|---|---|
| pH | $PO_4$ mg/l control | $PO_4$ mg/l filtrate | $PO_4$ mg/l adsorbed | $PO_4$ % adsorbed | $PO_4$ %/Fe (m/m Fe) adsorbed |
| 7.54 | 3985 | 3675 | 310 | 7.8 | 5.6 |

For all experiments, the iron content of the test solution was adjusted to 0.1M.

Comparative example Resovist ®: Phosphate adsorption in aqueous solution at pH 8.

| pH | $PO_4$ mg/l control | $PO_4$ mg/l filtrate | $PO_4$ mg/l adsorbed | $PO_4$ % adsorbed | $PO_4$ %/Fe (m/m Fe) adsorbed |
|---|---|---|---|---|---|
| 7.54 | 3985 | 3401 | 584 | 14.7 | 10.5 |

For all experiments, the iron content of the test solution was adjusted to 0.1M.

Comparative Example 5

An iron-hydroxide-based phosphate adsorbent was prepared according to production example 3 of WO 2006/000547 A2. This method describes the production of an iron-based phosphate adsorbent with optimized phosphate binding. However, in contrast to the method disclosed in WO 2006/000547 A2, we used inulin and gum arabic instead of starch.

A solution of 52 g sodium carbonate decahydrate (Sigma-Aldrich, No. 71538) in 78 g bidistilled water was prepared (solution 1). A second solution of 38 g iron(III) nitrate nonahydrate (Sigma-Aldrich, No. 31233) in 16 g bidistilled water was prepared (solution 2). Solution 2 was added dropwise to solution 1 with strong stirring over 30 min. The resulting solution (solution 3) was continued to stir for another 60 min at room temperature and then dialysed against water in a dialysis tube (Spectra Por dialysis tube, RC membrane, 12-14 kD cutoff). This procedure was continued until, after repeated exchange of water, conductivity in the filtrate was <0.5 mS/cm. A 100-ml aliquot was taken from the retentate, to which were successively added 3 g inulin (Sigma-Aldrich I2255, Chicory), 3 g gum arabic (Acaciabaum Reagent Grade, Sigma G9752), and 6 g sucrose (Sigma-Aldrich, No. S 7903). The red-brown turbit dispersion was reduced to 60 ml at 60° C. on a rotation vaporizer and dried overnight at 60° C. in a cabinet dryer. The resulting red-brown powder was ground with a mortar and pestle, yielding a fine powder with an iron content of 263.5 mg/g.

Comparative example 5: Phosphate adsorption in aqueous solution at different pHs.

| pH | $PO_4$ mg/l | $PO_4$ mg/l filtrate | $PO_4$ mg/l adsorbed | $PO_4$ % adsorbed | $PO_4$ %/Fe (m/m Fe) adsorbed |
|---|---|---|---|---|---|
| 3 | 3471 | 2251 | 1220 | 35.1 | 21.52 |
| 5.5 | 3705 | 2498 | 1207 | 32.58 | 21.38 |
| 8 | 3777 | 3119 | 658 | 17.42 | 11.48 |

For all experiments, the iron content of the test solution was adjusted to 0.1M.

Comparative Example 6

The precipitation of magnetite-maghemite iron oxide nanoparticles was prepared in a one-step synthesis in a mannose solution according to example 5 of WO 2007/095871 A2 (Horak).

10 ml of a 50 wt % D-mannose (Sigma-Aldrich, No. 63582) was mixed under stirring with 10 ml of an aqueous solution containing 1.51 g of iron(III) chloride hexahydrate (Sigma-Aldrich, No. 31232) and 0.64 g of iron(II) chloride tetrahydrate (Sigma-Aldrich, No. 44939). 7.5% aqueous ammonium hydroxide solution was slowly added (2 ml/min) under mild stirring until a pH 12 was reached, which was achieved after the addition of 16 ml of ammonium hydroxide. The mixture was then heated to 60° and maintained there for 15 min. After cooling to room temperature the mixture was sonicated at 860 W for 2 min (Sonorex Typ RK 156 BH, Bandelin GmbH, Berlin). The so obtained dispersion was dialyzed in tubes against water (12-14 kD cutoff, regenerated cellulose, Spectra Por) for 24 hours with a five time change of the water (2 l). The volume was reduced by evaporation an finally dried over night at 60° C. The so obtained powder has an iron content of 470 mg per gram dry material and a proportion of ferrous iron of 1.7% in relation to total iron by weight.

Comparative example 6: Phosphate adsorption in aqueous solution at different pHs.

| pH | $PO_4$ mg/l | $PO_4$ mg/l filtrate | $PO_4$ mg/l adsorbed | $PO_4$ % adsorbed | $PO_4$ %/Fe (m/m Fe) adsorbed |
|---|---|---|---|---|---|
| 3 | 3822 | 3627 | 195 | 5.1 | 3.4 |
| 5.5 | 3936 | 3747 | 189 | 4.8 | 3.4 |
| 8 | 3857 | 3726 | 131 | 3.4 | 2.3 |

For all experiments, the iron content of the test solution was adjusted to 0.1M.

Comparative example 6: Phosphate adsorption in Nutricomp MCT.

| pH | $PO_4$ mg/l control | $PO_4$ mg/l filtrate | $PO_4$ mg/l adsorbed | $PO_4$ % adsorbed | $PO_4$ %/Fe (m/m Fe) adsorbed |
|---|---|---|---|---|---|
| 7.54 | 6605 | 6058 | 547 | 9.7 | 10.0 |
| absolute free iron in filtrate as % of absolute iron input weight | | | | | 0.016 |

For all experiments, the iron content of the test solution was adjusted to 0.1M.

Comparative Example 7

The phosphate binding of the approved drug Renvela® with sevelamer carbonate as the active drug substance was tested in Nutricomp in a setting identical to iron-based phosphate adsorbers. Weight input of sevelamer carbonate was 197 mg absolute. This results in a molar ratio of 1:0.16 allyl-amine units:$PO_4$.

Comparative example 7: Phosphate adsorption in aqueous solution at pH 8.

| pH | $PO_4$ mg/l control | $PO_4$ mg/l filtrate | $PO_4$ mg/l adsorbed | $PO_4$ % adsorbed | $PO_4$ %/S (m/m Fe) adsorbed |
|---|---|---|---|---|---|
| 7.54 | 6821 | 4747 | 2074 | 30.4 | 10.5 |

S = sevelamer carbonate
For this experiment the absolute weight input of sevelamer carbonate was 197 mg

Comparative Example 8

A solube form of ferric citrate as the active drug substance of the phosphate binding oral drug drug Zerenex® (currently in clinical trials phase III) was prepared according to U.S. Pat. No. 7,767,851 B2 by Kwok et al. example 1.

5 M sodium hydroxide solution was added slowly added (10 ml per minute) to 27.3 ml of a 1.85M iron (III) chloride hexahydrate (Sigma-Aldrich, No. 31232) solution at room temperature until a pH of 7 was achieved (11 ml of 5 M sodium hydroxide was necessary). This mixture was sonicated at 860 W for 2 min (Sonorex Typ RK 156 BH, Bandelin GmbH, Berlin) to break up aggregates. This mixture was filtered using a folded cellulose paper filter (Rotilabo®-Faltenfilter, cellulose). The filtrate was centrifuged at 1500 rcf 10 min redispersed with water and centrifuged again, redispersion and centrifugation was repeated 3 more times. The supernatant was discarded and the remaining sediment was analyzed for iron content. 5% citric acid (weight/volume) was added to obtain a 1:1 molar ratio of iron ions:citrate and the mixture was heated to 80° C. under mild stirring. Further citric acid was subsequently added until a clear dark brown solution with an pH under 0.8 was obtained. This step takes 48 hours with stirring at 80° C. for 8 hours a day and rest overnight at room temperature. This dispersion was centrifuged at 1500 rcf for 15 min. The supernatant was mixed with 5 volumes of ethanol and under light stirring a pale beige precipitate was formed. This suspension was centrifuged at 1500 rcf for 10 minutes. The supernatant was discarded and the sediment was resuspended and centrifuged again with ethanol for two times. The precipitate was dried overnight at 60° C. and the resulting dry substance was ground to a fine powder with a mortar and pestle. It was not further sieved as described in U.S. Pat. No. 7,767,851 B2 by Kwok et al. example 1.

The final powder obtained in this way has an iron content of 226 mg/g and a proportion of ferrous iron of 3.79% in relation to total iron.

Comparative example 8: Phosphate adsorption in aqueous solution at different pHs.

| pH | $PO_4$ mg/l | $PO_4$ mg/l filtrate | $PO_4$ mg/l adsorbed | $PO_4$ % adsorbed | $PO_4$ %/Fe (m/m Fe) adsorbed |
|---|---|---|---|---|---|
| 3 | 3813 | 1184 | 2629 | 69.9 | 47.1 |
| 5.5 | 3918 | 1289 | 2629 | 67.1 | 47.2 |
| 8 | 3868 | 1491 | 2377 | 61.5 | 42.5 |

For all experiments, the iron content of the test solution was adjusted to 0.1M.

Comparative example 8: Phosphate adsorption in Nutricomp MCT.

| pH | $PO_4$ mg/l control | $PO_4$ mg/l filtrate | $PO_4$ mg/l adsorbed | $PO_4$ % adsorbed | $PO_4$ %/Fe (m/m Fe) adsorbed |
|---|---|---|---|---|---|
| 7.54 | 5982 | 2754 | 3228 | 54 | 57.7 |
| absolute free iron in filtrate as % of absolute iron input weight | | | | | 30.6 |

For all experiments, the iron content of the test solution was adjusted to 0.1M.

Comparative Example 9

To obtain a better soluble form of the commercially available iron citrate 30 g iron (III) citrate tribasic monohydrate (Fluka 44941) were dissolved in 200 ml bidistilled water at 90° C. After cooling to room temperature 150 ml pure ethanol was added. The resulting suspension was centrifuged at 1500 rcf for 10 min. The supernatant was withdrawn and the sediment was resuspended in 100 ml ethanol stirred for 5 min and centrifuged again. The sediment was air dried.

The final powder obtained in this way has an iron content of 218 mg/g and a proportion of ferrous iron of 5.3% in relation to total iron.

Comparative example 9: Phosphate adsorption in aqueous solution at different pHs.

| pH | $PO_4$ mg/l | $PO_4$ mg/l filtrate | $PO_4$ mg/l adsorbed | $PO_4$ % adsorbed | $PO_4$ %/Fe (m/m Fe) adsorbed |
|---|---|---|---|---|---|
| 3 | 3822 | 1035 | 2787 | 72.9 | 51.75 |
| 5.5 | 3936 | 1096 | 2839 | 72.14 | 52.38 |
| 8 | 38.57 | 1018 | 2839 | 73.62 | 52.66 |

For all experiments, the iron content of the test solution was adjusted to 0.1M.

Comparative example 9: Phosphate adsorption in Nutricomp MCT.

| pH | $PO_4$ mg/l control | $PO_4$ mg/l filtrate | $PO_4$ mg/l adsorbed | $PO_4$ % adsorbed | $PO_4$ %/Fe (m/m Fe) adsorbed |
|---|---|---|---|---|---|
| 7.54 | 6301 | 1702 | 4599 | 73 | 84 |
| absolute free iron in filtrate as % of absolute iron input weight | | | | | 17 |

For all experiments, the iron content of the test solution was adjusted to 0.1M.

Example 1

A phosphate adsorbent based on magnetite-maghemite was prepared by precipitation from a solution of ferrous and ferric iron in the presence of a base.

A solution was prepared by dissolving 7.55 g iron(III) chloride hexahydrate (Sigma-Aldrich, No. 31232) in 50 ml bidistilled water cooled to 4° C. (solution A). A second solution was prepared by dissolving 3.2 g iron(II) chloride tetrahydrate (Sigma-Aldrich, No. 44939) in solution A (solution B). A third solution was prepared by dissolving 25 g D-mannose (Sigma-Aldrich, No. 63582) in bidistilled water cooled to 4° C. (solution C). Solutions B and C were combined and stirred for 2 min (solution D). Solution D was supplemented with 100 ml of 1.5 M NaOH (cooled to 4° C.) and the resulting mixture stirred for 5 min at 4° C. until a homogeneous colloid was obtained (approx. 5 min). The colloid was then heated to 60° C. and stirred for 15 min at 60° C. Subsequently, the solution was cooled to room temperature while stirring over 15 min and reduced to 100 ml using ultrafiltration (10 kD, Spectrum, Hollow Fiber, PES). The solution was dialysed 5 times against 2 liters of bidistilled water in dialysis tubes (12-14 kD cutoff, regenerated cellulose, Spectra Por) until no more iron or chloride were detectable in the filtrate. The total amount of 200 ml colloid solution obtained after dialysis was mixed with 25 ml bidistilled water in which had been dissolved 0.1 g mannose, 3 g gum arabic (Acaciabaum Reagent Grade, Sigma G9752), and 3 g inulin (Sigma Aldrich I2255, Chicory), which had been dissolved together in 25 ml bidistilled water. This dispersion was stirred for 3 min and supplemented with 100% ethanol to yield 1l. This step precipitated the nanoparticles, which were removed by centrifugation at 800 rcf. The sediment was dried overnight at 60° C. The resulting dry substance was ground to a fine powder with a mortar and pestle.

The final powder has an iron content of 157 mg/g dry substance and a proportion of ferrous iron of 2.04% in relation to total iron.

Comparative example 9: Phosphate adsorption in aqueous solution at different pHs.

| pH | PO$_4$ mg/l | PO$_4$ mg/l filtrate | PO$_4$ mg/l adsorbed | PO$_4$ % adsorbed | PO$_4$ %/Fe (m/m Fe) adsorbed |
|---|---|---|---|---|---|
| 3 | 4136 | 690 | 3446 | 83.1 | 67.65 |
| 5.5 | 4109 | 981 | 31.28 | 76.1 | 61.51 |
| 8 | 4120 | 2384 | 1735 | 42.1 | 32.12 |

For all experiments, the iron content of the test solution was adjusted to 0.1M.

Example 1: Phosphate adsorption in Nutricomp MCT.

| pH | PO$_4$ mg/l control | PO$_4$ mg/l filtrate | PO$_4$ mg/l adsorbed | PO$_4$ % adsorbed | PO$_4$ %/Fe (m/m Fe) adsorbed |
|---|---|---|---|---|---|
| 7.54 | 6870 | 3302 | 3568 | 51.9 | 63.2 |
| absolute free iron in filtrate as % of absolute iron input weight | | | | | 1.8 |

For all experiments, the iron content of the test solution was adjusted to 0.1M.

Example 1B

The production of example 1B is identical to the production according to example 1 except that the individual steps are not performed with cooled solutions. All steps in preparing the phosphate adsorbent according to example 1B were performed at room temperature. The iron oxide powder prepared according to example 1B has a total iron content of 250 mg with a 5.28% proportion of ferrous iron relative to total iron (weight/weight).

Example 1 B: Phosphate adsorption in Nutricomp MCT.

| pH | PO$_4$ mg/l control | PO$_4$ mg/l filtrate | PO$_4$ mg/l adsorbed | PO$_4$ % adsorbed | PO$_4$ %/Fe (m/m Fe) adsorbed |
|---|---|---|---|---|---|
| 7.54 | 6870 | 4371 | 2499 | 36.4 | 44.57 |

For all experiments, the iron content of the test solution was adjusted to 0.1M.

Example 2

A phosphate adsorbent based on magnetite-maghemite was prepared by precipitation from a solution of ferrous and ferric iron in the presence of a base. A solution was prepared by dissolving 7.2 g iron(III) chloride hexahydrate (Sigma-Aldrich, No. 31232) and 10 g D-mannose (Sigma-Aldrich, No. 63582) in 25 ml 0.4 M hydrochloric acid with a temperature of 4° C. (solution A). Solution B was prepared by adding 3.5 g iron(II) chloride tetrahydrate (Sigma-Aldrich, No. 44939) to solution A. Solution B was stirred at 4° C. for 5 min. Solution B was rapidly added to 80 ml of 1.5 M hydrochloric acid (solution C). Solution C was stirred at 4° C. until a black-brown suspension was obtained. Then solution C was heated to 60° C. and stirred at this temperature for another 30 min. This dispersion was supplemented by 3 g inulin (Sigma-Aldrich I2255, Chicory) and stirred for another 3 min. The dispersion was removed from the hotplate and stirred at room temperature until it was cooled to room temperature. This dispersion was centrifuged at 1500 rcf for 10 min. The sediment was dispersed with five times its volume of 3% inulin solution and centrifuged under said conditions. This step was repeated 5 times. The final sediment obtained after completion of centrifugation was dried overnight at 60° C. The resulting granulate was ground to a fine powder with a mortar and pestle.

The final powder obtained in this way has an iron content of 307 mg/g and a proportion of ferrous iron of 9.57% in relation to total iron.

Example 2: Phosphate adsorption in aqueous solution at different pHs.

| pH | PO$_4$ mg/l | PO$_4$ mg/l filtrate | PO$_4$ mg/l adsorbed | PO$_4$ % adsorbed | PO$_4$ %/Fe (m/m Fe) adsorbed |
|---|---|---|---|---|---|
| 3 | 3212 | 1628 | 1584 | 49.3 | 28.2 |
| 5.5 | 3312 | 1852 | 1461 | 44.1 | 25.91 |
| 8 | 3395 | 2355 | 1040 | 30.63 | 18.69 |

For all experiments, the iron content of the test solution was adjusted to 0.1M.

Example 2: Phosphate adsorption in Nutricomp MCT.

| pH | PO$_4$ mg/l control | PO$_4$ mg/l filtrate | PO$_4$ mg/l adsorbed | PO$_4$ % adsorbed | PO$_4$ %/Fe (m/m Fe) adsorbed |
|---|---|---|---|---|---|
| 7.54 | 7468 | 4863 | 2606 | 34.9 | 47.51 |

For all experiments, the iron content of the test solution was adjusted to 0.1M.

Example 3

A phosphate adsorbent based on magnetite-maghemite was prepared by precipitation from a solution of ferrous and ferric iron in the presence of a base. A solution was prepared by dissolving 7.2 g iron(III) chloride hexahydrate (Sigma-Aldrich, No. 31232) in 25 ml 0.4 M hydrochloric acid with a temperature of 4° C. (solution A). Solution B was prepared by adding 3.5 g iron(II) chloride tetrahydrate (Sigma-Aldrich, No. 44939) to solution A. Ten grams of mannitol (Sigma-Aldrich, No. M 4125) were dissolved in 80 ml of 1.5 M sodium hydroxide solution (solution C). Solution B was rapidly added to solution C, and the mixture was stirred at 4° C. until a black-brown suspension was obtained. This suspension was supplemented by 3 g of potato starch (Sigma-Aldrich, No. S4251) and heated to 60° C. while stirring. To this suspension was added 5 ml 30% hydrogen peroxide in 1-ml amounts, stirring for 1 min at 60° C. after each addition. Five minutes after the last addition, the absence of peroxidase was demonstrated using the Quantofix Peroxid 100 test (Merck KdA). The suspension obtained in this way was supplemented by 3 g inulin (Sigma Aldrich I2255, Chicory), and the resulting suspension was continued to stir without further heating until it was cooled to room temperature (approx. 20 min). After cooling, 3 g of carboxymethyl cellulose was added (Sigma-Aldrich, No. C9481, USP grade). The resulting suspension was centrifuged (1500 rcf, 10 min). The sediment was resuspended with five times its volume of 2% saccharose solution and centrifuged. This step was repeated four times. The resulting sediments was dried overnight at 60° C. in an oven. The resulting granulate was ground to a fine powder with a mortar and pestle.

The final iron oxide powder has an iron content of 298.03 mg/g and a proportion of ferrous iron of 11.18% in relation to the total iron content (weight/weight).

Example 3: Phosphate adsorption in aqueous solution at different pHs.

| pH | PO$_4$ mg/l | PO$_4$ mg/l filtrate | PO$_4$ mg/l adsorbed | PO$_4$ % adsorbed | PO$_4$ %/Fe (m/m Fe) adsorbed |
|---|---|---|---|---|---|
| 3 | 3725 | 1963 | 1742 | 46.8 | 32.21 |
| 5.5 | 37.62 | 2107 | 1655 | 43.99 | 29.51 |
| 8 | 3809 | 2716 | 1093 | 28.7 | 19.4 |

For all experiments, the iron content of the test solution was adjusted to 0.1M.

Example 3: Phosphate adsorption in Nutricomp MCT.

| pH | PO$_4$ mg/l control | PO$_4$ mg/l filtrate | PO$_4$ mg/l adsorbed | PO$_4$ % adsorbed | PO$_4$ %/Fe (m/m Fe) adsorbed |
|---|---|---|---|---|---|
| 7.54 | 7468 | 4854 | 2614 | 35 | 47.88 |

For all experiments, the iron content of the test solution was adjusted to 0.1M.

Example 4

A phosphate adsorbent based on magnetite-maghemite was prepared by precipitation from a solution of ferrous and ferric iron in the presence of a base. A solution was prepared by dissolving 7.2 g iron(III) chloride hexahydrate (Sigma-Aldrich, No. 31232) in 25 ml 0.4 M hydrochloric acid with a temperature of 4° C. (solution A). Solution B was prepared by adding 3.5 g iron(II) chloride tetrahydrate (Sigma-Aldrich, No. 44939) to solution A. Ten grams of saccharose (Sigma-Aldrich, No. S0389) were dissolved in 80 ml of 1.5 M sodium hydroxide solution (solution C). Solution B was rapidly added to solution C and the mixture was stirred at 4° C. until a black-brown suspension was obtained. This suspension was supplemented by 3 g of potato starch (Sigma-Aldrich, No. A4251) and heated to 60° C. while stirring. To this suspension was added 5 ml of 30% hydrogen peroxide in 1-ml amounts, stifling for 1 min at 60° C. after each addition. Five minutes after the last addition, the absence of perioxidase was demonstrated using the Quantofix Peroxid 100 test (Merck KdA). The suspension obtained in this way was supplemented by 3 g inulin (Sigma Aldrich I2255, Chicory), and the resulting suspension was continued to stir without further heating until it was cooled to room temperature (approx. 20 min). After cooling, 3 g of carboxymethyl cellulose was added (Sigma-Aldrich, No. C9481, USP grade). The resulting suspension was centrifuged (1500 rcf, 10 min). The sediment was resuspended with five times its volume of 2% saccharose solution and centrifuged. This step was repeated four times. The resulting sediments was dried overnight at 60° C. in an oven. The resulting granulate was ground to a fine powder with a mortar and pestle.

The resulting iron oxide powder has an iron content of 353.51 mg/g and a proportion of ferrous iron of 4.73% in relation to total iron (weight/weight).

Example 4: Phosphate adsorption in aqueous solution at different pHs.

| pH | PO$_4$ mg/l | PO$_4$ mg/l filtrate | PO$_4$ mg/l adsorbed | PO$_4$ % adsorbed | PO$_4$ %/Fe (m/m Fe) adsorbed |
|---|---|---|---|---|---|
| 3 | 3725 | 2564 | 1161 | 46.8 | 31.2 |
| 5.5 | 3762 | 2809 | 953 | 25.33 | 17.06 |
| 8 | 3809 | 3177 | 632 | 16.59 | 11.32 |

For all experiments, the iron content of the test solution was adjusted to 0.1M.

Example 4: Phosphate adsorption in Nutricomp MCT.

| pH | PO$_4$ mg/l control | PO$_4$ mg/l filtrate | PO$_4$ mg/l adsorbed | PO$_4$ % adsorbed | PO$_4$ %/Fe (m/m Fe) adsorbed |
|---|---|---|---|---|---|
| 7.54 | 7468 | 5784 | 1684 | 22.5 | 29.83 |

For all experiments, the iron content of the test solution was adjusted to 0.1M.

Example 5

Using the production procedure of example 1, we tested different combinations of primary coating and secondary excipients with regard to phosphate adsorption.

In all cases, solutions were prepared using 50 ml of 0.4 M hydrochloric acid, in which 14.4 g iron(III) chloride hexahydrate (Sigma-Aldrich No. 31232) and 7 g iron(II) chloride tetrahydrate (Sigma-Aldrich No. 44939) were dissolved in conjunction with the primary coating material as listed in the "Primary coating" column in the table below (solution A). Solution A was abruptly added to 80 ml ice-cooled 1.5 M sodium hydroxide solution and stirred for 5 min. The resulting suspension was supplemented with the respective excipient as listed in the "Excipients" column of the table below. The resulting suspension was stirred for 30 min in an iced waterbath. Thereafter, 2 ml of 15% hydrogen peroxide was added to the suspension. The resulting dispersion was heated to 65° C. and stirred at this temperature for 15 min. After cooling to room temperature, the suspension obtained in this way was centrifuged (10 min at 1500 rcf), the supernatant discarded, and the sediment dried overnight at 60° C.

Example 5: Phosphate adsorption in aqueous 40 mM phosphate solution at pH 5.

| | Primary coating | Excipient | PO4 %/Fe (m/m Fe) adsorbed |
|---|---|---|---|
| Example 5 a | Carmellose 15 g | 2 g inulin<br>2 g gum arabic<br>2 g starch | 30.3% |
| Example 5b | None | 3 g gum arabic | 11.2% |
| Example 5c | Lecithin 5 g | 2 g gum arabic<br>2 g starch | 12.5% |
| Example 5d | Carmellose 15 g | 2 g gum arabic<br>2 g starch | 14.3% |
| Example 5e | Maltodextrin 15 g | None | 13.2% |
| Example 5f | Mannitol 15 g | None | 9.6% |
| Example 5g | Mannitol 15 g | 3 g inulin<br>3 g gum arabic | 34.8% |

For all experiments, the iron content of the test solution was adjusted to 0.1M.

Example 6

A phosphate adsorbent based on magnetite-maghemite was prepared by precipitation from a solution of ferrous and ferric iron in the presence of a base. A solution was prepared by dissolving 7.2 g iron(III) chloride hexahydrate (Sigma-Aldrich, No. 31232) in 25 ml 0.4 M hydrochloric acid with a temperature of 4° C. (solution A). Solution B was prepared by adding 3.5 g iron(II) chloride tetrahydrate (Sigma-Aldrich, No. 44939) to solution A. Solution B was supplemented by 70 ml of 1.5 M sodium hydroxide solution (cooled to 4° C.) and the mixture stirred at 4° C. until a black-brown suspension was obtained. This black-brown suspension was supplemented by 2 ml 30% hydrogen peroxide, the suspension heated to 75° C., and the suspension was kept at this temperature with free exposure to ambient air for 10 min. After cooling to room temperature, the suspension was tested for the absence of peroxides using the Quantofix Peroxid 100 test (Merck KdA).

The suspension obtained in this way was successively supplemented by 3 g potato starch (Sigma-Aldrich, No. S4251) and 3 g gum arabic (acacia tree, Reagent Grade, Sigma G9752), each dissolved in 15 ml 1.5 M NaOH waiting 5 min after each addition. Moreover, 4 g inulin and 3 g inulin (Sigma Aldrich I2255, Chicory) and 0.1 g carboxymethyl cellulose sodium were successively added as powders, stirring for 5 min after each addition. This suspension was centrifuged at 700 rcf for 15 min and the supernatant discarded; the resulting sediment was resuspended with 30 ml 2% sucrose solution and centrifuged this step was repeated 5 times.

The sediment was dried overnight at 60° C. in an oven. The resulting granulate was ground to a fine powder with a mortar and pestle.

The final iron oxide powder has an iron content of 207 mg/g with a proportion of ferrous iron of 3.13% relative to the total iron content (weight/weight).

Example 6: Phosphate adsorption in Nutricomp MCT.

| pH | $PO_4$ mg/l control | $PO_4$ mg/l filtrate | $PO_4$ mg/l adsorbed | $PO_4$ % adsorbed | $PO_4$ %/Fe (m/m Fe) adsorbed |
|---|---|---|---|---|---|
| 7.54 | 7468 | 4773 | 2495 | 33.4 | 44.59 |

For all experiments, the iron content of the test solution was adjusted to 0.1M.

Example 7

A solution was prepared by dissolving 7.55 g iron(III) chloride hexahydrate (Sigma-Aldrich, No. 31232) in 25 ml bidistilled water at 4° C. (solution A). Solution B was prepared by adding 3.2 g iron(II) chloride tetrahydrate (Sigma-Aldrich, No. 44939) to solution A. Solution C was prepared by dissolving 15 g D-Mannitol (Sigma-Aldrich, No. M 4125) in 100 ml 1.5 M NaOH cooled to 4° C. Solution B was decanted to solution C under stifling. This mixture was stirred at 4° C. until a black brown precipitate was formed. 7.5 g inulin (Sigma Aldrich I2255, Chicory) were added and this mixture was stirred for further 15 min at 4° C. After addition of 3 ml 30% hydrogen peroxide the mixture was heated to 60° C., and stirred at this temperature for further 15 min. After cooling to room temperature the suspension was tested for the absence of peroxides using the Quantofix Peroxid 100 test (Merck KdA). The so obtained colloid was dialysed against water using cellulose tube (3.5 kD cutoff, Spectra Por dialysis tube, RC membrane) the suspension was kept at this temperature with free exposure to ambient air for 10 min. The retentate was centrifuged (1500 rcf, 10 min). The sediment was withdrawn and the supernatant was supplemented with 3 g arabic gum. The so obtained dispersion was lyophilized.

The final iron oxide powder has an iron content of 211 mg/g with a proportion of ferrous iron of 0.89% relative to the total iron content (weight/weight).

Two phosphate binding experiments have been performed; example 7A with the above obtained powder, example 7B by addition of ascorbic acid to the final powder according to example 7B.

To test the influence of ascorbic acid on the phosphate adsorption efficacy in Nutricomp 200 mg of the substance was grinded with ascorbic acid and binding experiments were performed in Nutricomp MCT (example 7b).

In example 7c, the pH was adjusted during the incubation of the substance in Nutricomp MCT using HCl without ascorbic acid.

In example 7d the influence of the mixture of gelatine gel on the phosphate adsorption capacity was tested.

Example 7a: Phosphate adsorption in Nutricomp MCT.

| pH | $PO_4$ mg/l control | $PO_4$ mg/l filtrate | $PO_4$ mg/l adsorbed | $PO_4$ % adsorbed | $PO_4$ %/Fe (m/m Fe) adsorbed |
|---|---|---|---|---|---|
| 7.50 | 6105 | 3365 | 2740 | 44.9 | 45.36 |
| absolute free iron in filtrate as % of absolute iron input weight | | | | | 0.67 |

For all experiments, the iron content of the test solution was adjusted to 0.1M.

Example 7b: Phosphate adsorption in Nutricomp MCT - in ascorbic acid

| pH ascorbic acid | $PO_4$ mg/l control | $PO_4$ mg/l filtrate | $PO_4$ mg/l adsorbed | $PO_4$ % adsorbed | $PO_4$ %/Fe (m/m Fe) adsorbed |
|---|---|---|---|---|---|
| 7.00 | | | | | |
| 10 mg | 8947 | 2030 | 6017 | 67.3 | 112.4 |
| 50 mg | 8947 | 1754 | 7192 | 80.4 | 131.2 |
| absolute free iron in filtrate as % of absolute iron input weight 10 mg | | | | | 0.56 |
| absolute free iron in filtrate as % of absolute iron input weight 50 mg | | | | | 0.47 |

For all experiments, the iron content of the test solution was adjusted to 0.1M.
The pH of Nutricomp was adjusted to 7.54 before addition of the adsorbens with ascorbic acid; a pH of 7.0 was achieved at the end of the incubation period.

Example 7c: Phosphate adsorption in Nutricomp MCT - with hydrochloric acid

| pH | $PO_4$ mg/l control | $PO_4$ mg/l filtrate | $PO_4$ mg/l adsorbed | $PO_4$ % adsorbed | $PO_4$ %/Fe (m/m Fe) adsorbed |
|---|---|---|---|---|---|
| 7.00 | 6105 | 1684 | 3549 | 67.8 | 58.35 |
| absolute free iron in filtrate as % of absolute iron input weight | | | | | 0.35 |

For all experiments, the iron content of the test solution was adjusted to 0.1M.
The pH of Nutricomp was adjusted to 7.54 before addition of the adsorbens with ascorbic acid; a pH of 7.0 was achieved at the end of the incubation period by titration with hydrochloric acid Example 7d: Phosphate adsorption
in Nutricomp MCT - with gelatin

| pH | PO$_4$ mg/l control | PO$_4$ mg/l filtrate | PO$_4$ mg/l adsorbed | PO$_4$ % adsorbed | PO$_4$ %/Fe (m/m Fe) adsorbed |
| --- | --- | --- | --- | --- | --- |
| 7.00 | 8237 | 2965 | 5272 | 64 | 114 |
| absolute free iron in filtrate as % of absolute iron input weight | | | | | 0.28 |

For all experiments, the iron content of the test solution was adjusted to 0.1M.
The pH of Nutricomp was adjusted to 7.54 before addition of the adsorbens with ascorbic acid; a pH of 7.0 was achieved at the end of the incubation period by titration with hydrochloric acid Example 8

Phosphate adsorption in fetal calf serum.

An amount of 0.06 mmol relative to iron from example 1 was dissolved in 10 ml fetal calf serum. For comparison, an identical experiment was performed with Feraheme, i.e., iron oxide stabilized with carboxymethyl dextran. These samples were incubated at 37° C. for two hours and then centrifuged using a centrifuge filter with 30 kD cutoff. In the filtrate, phosphate content was determined according to the preceding examples.

Example 7: Phosphate adsorption in serum

| Sample | PO$_4$ mg/l control | PO$_4$ mg/l filtrate | PO$_4$ mg/l adsorbed | PO$_4$ % adsorbed | PO$_4$ %/Fe (m/m Fe) adsorbed |
| --- | --- | --- | --- | --- | --- |
| Example 1 | 251.59 | 173.9 | 77.69 | 30.9 | 24.79 |
| Feraheme | 259.51 | 244.34 | 7.25 | 2.9 | 2.37 |

For all experiments, the iron content of the test solution was adjusted to 6 mM.

Maghemite-Based Nanoparticles as an Efficient New Oral Phosphate Adsorber: Preclinical in Vivo Results in Rats Comparison of Example 7 of WO 2013/034267 A1 with Sevelamer Purpose:

Hyperphosphatemia is the main cause of cardiovascular mortality in patients with impaired renal function. Currently approved oral phosphate-lowering drugs fail to achieve the NKF-KDOQI™-recommended target phosphate serum level in 40% of patients (Block et. al: Association of serum phosphorus and calcium×phosphate product with mortality risk in chronic hemodialysis patients: a national study. American Journal of Kidney Disease, Vol 31, No 4 (April), 1998: 607-617). This could be explained by a high pill burden linked to adverse reactions like diarrhea as well as obstipation and nausea.

Calcium based phosphate adsorber accelerate cardiovascular calcifications and the risk for an increased cardiovascular morbidity and mortality.

Hence, there is a clinical need for more efficient oral phosphate-lowering drugs. Currently the non-metal based phosphate adsorber sevelamer carbonate (active substance of Renvela®, Genzyme Corporation) or sevelamer hydrochloride (active substance of Renagel®, Genzyme Corporation) is the gold standard in therapy of elevated phosphate serum levels.

In rats the in vivo enteral phosphate-adsorbing efficacy of new maghemite-based phosphate adsorber according to present WO 2013/034267 A1, Example 7 (herein named "C-PAM-11"—Charité-Phosphate-Adsorbing-Maghemite) was compared to the commercially available drug Renvela® with sevelamer carbonate as the active substance.

Materials and Methods

For the in vivo experiments Example 7 of the present application was chosen because with the use of gelatin the drug product according to Example 7 and the reference drug Renvela® could well be mixed with the rat standard diet and it was rated by a self test of the inventors as completely tasteless. This is a basic requirement for the acceptance by the animals and it has been demonstrated that the addition of gelatin increased the phosphate adsorbing efficacy.

In detail, 500 g of the powder form of the rat diet (Altromin 1320, 0.7% phosphorus content) was mixed with 500 ml 5% gelatin from porcine skin, Fa. Sigma, Type A. Food balls of 20 gram each were formed. Food was stored for a maximum of three days at 4° C. Rats were controlled daily and food residues were removed and replaced by fresh food balls each day.

Over a 4-week period healthy Sprague Dawley rats (n=8 per group, CD rat Charles River, Sulzfeld Germany) were fed ad libitum this gelatin rat diet food balls as control (group A), or gelatin rat diet balls supplemented with Renvela® (group B) or C-PAM-11 (group C) as treatment groups (supplementation: 0.5% weight/weight based on sevelamer or iron). Once a week the rats were housed in individual metabolic cages for 24 hours to collect urine. After the 4-week period rats were sacrificed for blood chemistry and histology of organs and the gastrointestinal tract. Furthermore the femora were gained to measure the bone density by using a High Resolution Peripheral Quantitative Computer Tomography (HR pQCT).

Results and Discussion

All groups tolerated the procedure well. Food intake of all rats groups differs not significantly between the groups and was overall higher compared to Charles River breeder data. Weight increase (from an average of 289±26 g) was significantly higher in group B (467±31 g) than in groups A (438±30 g) and C (420±27 g). Weight increase lies within the breeder data range and was exceeded by the group B (Renvela®). Urine phosphate excretion was significantly lower in group C versus A and B at all sampling times (FIG. 2). At 4 week treatment time the 24 hours urine phosphate excretion was 0.075±0.089 mg (C) versus 6.59±7.15 mg (A) and 0.48±0.55 mg (B). Group C developed hypophosphatemia with serum phosphate of 1.9±0.09 mmol/l versus 2.5±0.4 mmol/l in group A and 2.4±0.41 mmol/l in group B. All other blood chemistry parameters were normal. Histology revealed no abnormalities in any group. The HR pQCT measurements detected a significantly lower bone density in Group C revealing an osteomalacia in these animals which could be explained by the extreme enteral phosphate-adsorbing efficacy of the new maghemite-based nanoparticles. This is an unwanted adverse effect which simply could be prevented by further dose reduction.

Currently no data are published with approved phosphate binders or phosphate binders in experimental or clinical research and development showing such a tremendous phosphate binding capacity in the gastrointestinal tract which induces a marked hypophosphatemia in healthy rats, as it has been found for this new type of high and pure crystalline maghemite nanoparticles as laid down in the above mentioned patent.

REFERENCES

Theresa M. Barber. 2002. Phosphate adsorption by mixed and reduced iron phases in static and dynamic systems. Department of Geology. Stanford University. Stanford, Calif., USA)

Brambilla et al. Gadolinium and Lanthanum: A iatrogenic transmetallation; Clinical Biochemistry; 2008; 41: 1029-1033.

Coladonato, Journal of American Society of Nephrology 2005, 16, 107-144.

Daou et al., Chemistry of Materials 2007, 19, 4494-4505.

Heinrich, Intestinal absorption of 59Fe from neutron-activated commercial oral iron(III)-citrate and iron(III)-hydroxide-polymaltose complexes in man, Arzneimittelforschung, 1987, 37(1A): 105-107

Hruska et al., Kidney International 2008, 74, 148-157.

Hsu et al. New Phosphate Binding Agents: Ferric Compounds; Journal of American Society of Nephrology; 1999; 10: 1274-1280

Sahoo et al. 2005, Aqueous ferrofluid of magnetic nanoparticles: Fluorescence Labeling and magnetophoretic control. Journal of Physical Chemistry 2005, 109, 3879-3885.

Somers, Relative Oral Toxicity of Some Therapeutic Iron Preparations, British Medical Journal, 1947, August, 201-203

Wills M R, Savory J. Aluminum and chronic renal failure: sources, absorption, transport, and toxicity. Crit Rev Clin Lab Sci 1989; 27: 59-107

The invention claimed is:

1. A phosphate adsorbent comprising
   (i) an iron oxide core comprising a crystal structure of inverse spinel iron oxide,
   (ii) a coating selected from (a) mono- or disaccharides or (b) alditols or mixtures thereof,
   and
   (iii) a pharmaceutical excipient that is a polymeric carbohydrate,
   wherein the phosphate adsorbent has the form of nanoparticles with a particle size of the iron oxide core of less than 20 nm, wherein an iron content is about 3 to 50 wt-% of total weight of the phosphate adsorbent and wherein said phosphate adsorbent has a phosphate-binding capacity of at least 300 mg of adsorbed phosphate per gram of iron,
   and wherein said phosphate adsorbent has an iron release of less than 10% of the total iron input in a standardized food suspension at pH 7.54 to which the phosphate adsorbent is added.

2. The phosphate adsorbent of claim 1, wherein the phosphate adsorbent is monocrystalline.

3. The phosphate adsorbent according to claim 1 or 2, wherein the coating (ii) comprises mono- or disaccharides of aliphatic or aromatic hexoses or pentoses, or wherein the coating (ii) comprises alditol(s) (b) selected from the group consisting of: mannitol, sorbitol, isomalt, threitol, lactitol, xylitol, arabitol, erythritol, and glycerol.

4. The phosphate adsorbent according to claim 1, wherein the coating (ii) is present in molar excess in relation to the available binding sites on the iron oxide crystal surfaces of the iron oxide cores (i).

5. The phosphate adsorbent according to claim 1, wherein the pharmaceutical excipient (iii) is selected from the group consisting of:
   glucans,
   carboxymethyl cellulose,
   fructans,
   gum arabic,
   and mixtures thereof.

6. The phosphate adsorbent according to claim 1, further comprising ascorbic acid.

7. The phosphate adsorbent according to claim 1 obtained by a method comprising alkaline precipitation of iron(II) and iron(III) salt solutions with a base, which is selected from NaOH, KOH, or ammonium hydroxide or mixtures thereof, in the presence of a compound selected from (a) mono- or disaccharides or (b) alditols or mixtures thereof, wherein alkaline precipitation is performed at a temperature of 0 to 20° C.

8. A pharmaceutical composition comprising
   a phosphate adsorbent according to claim 1, and
   optionally, a pharmaceutical excipient,
   optionally, one or more further active ingredients, and
   optionally, a pharmaceutical vehicle.

9. The pharmaceutical composition of claim 8, wherein the pharmaceutical excipient is selected from the group consisting of: fructans, and a mixture of a fructan and gum arabic.

10. The pharmaceutical composition according to claim 8 or 9, comprising ascorbic acid as further active ingredient.

11. The pharmaceutical composition according to claim 8 or 9, comprising gelatine as a pharmaceutical vehicle.

12. The pharmaceutical composition according to claim 11 in a dosage form selected from granules, tablets, capsules, pills, lozenges, chewable tablets, chewing gum, fruit gum, powder for solution, solutions, dispersions, suspensions, emulsions, and gels.

13. The phosphate adsorbent according to claim 1 or the pharmaceutical composition according to claim 8 or 9 for use as a pharmaceutical.

14. The phosphate adsorbent according to claim 1 or the pharmaceutical composition according to claim 8 or 9 for prevention or treatment of hyperphosphatemia.

15. The phosphate adsorbent according to claim 1 or the pharmaceutical composition according to claim 8 or 9 for
   selective removal or elimination of inorganic phosphate from body fluids or from foods,
   lowering of serum phosphate levels,
   removal of phosphate from saliva,
   maintaining a physiological (serum) phosphate level in a subject in need of such treatment,
   or for short-term lowering of the serum phosphate level.

16. The phosphate adsorbent according to claim 1 or the pharmaceutical composition according to claim 8 or 9 for prevention or treatment of hyperphosphatemia in a subject, wherein the subject is a human or an animal.

17. The phosphate adsorbent according to claim 1 or 2, wherein the coating (ii) comprises mono- or disaccharides (a) selected from the group consisting of: mannose, saccharose, fructose, fucose, trehalose, glucose, rhamnose, galactose, maltose, and arabinose.

18. The phosphate adsorbent according to claim 1, wherein the pharmaceutical excipient (iii) is a mixture of at least one fructan and gum arabic.

19. The phosphate adsorbent according to claim 18, wherein the pharmaceutical excipient (iii) is a mixture of inulin and gum arabic.

20. The pharmaceutical composition according to claim 11, wherein the gelatine has a gel strength between 10 and 300 Bloom gel strength units.

21. The pharmaceutical composition according to claim 8, wherein said pharmaceutical composition is in an oral dosage form.

22. The pharmaceutical composition according to claim 8 or 9 for prevention or treatment of hyperphosphatemia in a dosage form for oral or parenteral administration.

23. The phosphate adsorbent of claim 1, wherein the amount of iron release is determined by reduction of iron ions to ferrous iron within a filtrate of a standardized food suspension to simulate gastric contents to which the phosphate adsorbent is added.

* * * * *